(12) United States Patent
Chourasia et al.

(10) Patent No.: US 12,323,773 B2
(45) Date of Patent: Jun. 3, 2025

(54) MANAGING AUDIO CONTENT DELIVERY

(71) Applicant: SAMSUNG ELECTRONICS CO., LTD., Suwon-si (KR)

(72) Inventors: Amod Ashok Chourasia, Uttar Pradesh (IN); Choice Choudhary, Uttar Pradesh (IN); Sobita Choudhary, Uttar Pradesh (IN)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 307 days.

(21) Appl. No.: 17/865,465

(22) Filed: Jul. 15, 2022

(65) Prior Publication Data

US 2023/0081796 A1 Mar. 16, 2023

Related U.S. Application Data

(63) Continuation of application No. PCT/KR2022/007986, filed on Jun. 7, 2022.

(30) Foreign Application Priority Data

Sep. 9, 2021 (IN) .............................. 202141040875

(51) Int. Cl.
*H04R 25/00* (2006.01)
*A61B 5/021* (2006.01)
(Continued)

(52) U.S. Cl.
CPC .............. *H04R 25/75* (2013.01); *H04R 3/00* (2013.01); *H04R 29/001* (2013.01); *A61B 5/021* (2013.01);
(Continued)

(58) Field of Classification Search
CPC ........ H04R 25/75; H04R 3/00; H04R 29/001; G10H 20/70; G16H 50/25; A61B 5/021;
(Continued)

(56) References Cited

U.S. PATENT DOCUMENTS 6,682,472 B1    1/2004   Davis
8,494,507 B1 *   7/2013   Tedesco ................. G09B 21/00
                                                    455/418
(Continued)

FOREIGN PATENT DOCUMENTS

CN    110613459 A    12/2019
CN    211089903 U    7/2020
(Continued)

OTHER PUBLICATIONS

Indian Examination Report for Indian Patent Application No. 202141040875, Filing Date: Sep. 9, 2021; Issued: May 3, 2023.
(Continued)

*Primary Examiner* — Carolyn R Edwards
*Assistant Examiner* — Kuassi A Ganmavo
(74) *Attorney, Agent, or Firm* — CANTOR COLBURN LLP

(57) ABSTRACT

Embodiments are directed to a method and an electronic device (100) for managing audio content delivery by an audio content delivery device (100). The method includes detecting, by the audio content delivery device (100), a buzzing sound in a user's ear during output of an audio content. The audio content delivery device (100) categorizes the buzzing sound, for example, as a subjective buzzing or an objective buzzing. Further, the audio content delivery device (100) computes a user experience score and generates a modified audio content based the user experience score. The modified audio content is based on the buzzing sound and the audio content. The audio content delivery device (100) outputs the modified audio content depending on the user experience score.

15 Claims, 21 Drawing Sheets

(51) Int. Cl.
   *A61B 5/024* (2006.01)
   *A61M 21/00* (2006.01)
   *A61M 21/02* (2006.01)
   *H04R 3/00* (2006.01)
   *H04R 29/00* (2006.01)

(52) U.S. Cl.
   CPC .............. *A61B 5/024* (2013.01); *A61M 21/00* (2013.01); *A61M 2021/0027* (2013.01); *A61M 21/02* (2013.01); *A61M 2205/18* (2013.01); *A61M 2205/581* (2013.01)

(58) Field of Classification Search
   CPC ........ A61B 5/024; A61B 5/128; A61M 21/00; A61M 21/02; A61M 2021/0027; A61M 2205/18; A61M 2205/3358; A61M 2205/3375; A61M 2205/3592; A61M 2205/505; A61M 2205/52; A61M 2205/581; A61M 2209/088; A61M 2230/30
   See application file for complete search history.

(56) References Cited

U.S. PATENT DOCUMENTS

| | | | |
|---|---|---|---|
| 8,979,729 | B2 | 3/2015 | Davis |
| 9,445,183 | B2 | 9/2016 | Dahl |
| 10,987,249 | B2 | 4/2021 | O'Neill et al. |
| 11,228,854 | B2 | 1/2022 | Noda |
| 2002/0090100 | A1* | 7/2002 | Thiede ............... H04R 25/75 381/314 |
| 2004/0059251 | A1 | 3/2004 | Choy |
| 2009/0163828 | A1* | 6/2009 | Turner ................ A61B 5/38 600/559 |
| 2011/0054241 | A1* | 3/2011 | Jensen ............... H04R 25/75 600/28 |
| 2013/0129097 | A1* | 5/2013 | Park .................. H04M 1/24 381/56 |
| 2013/0204170 | A1* | 8/2013 | Zeng ................. A61B 5/128 601/47 |
| 2014/0288685 | A1* | 9/2014 | Haefeli ............... G06F 16/60 700/94 |
| 2015/0005661 | A1 | 1/2015 | Trammell |
| 2015/0073296 | A1* | 3/2015 | Zeng ................. A61B 5/128 600/559 |
| 2015/0372650 | A1* | 12/2015 | Thormundsson .... H03G 11/008 381/94.1 |
| 2016/0051150 | A1* | 2/2016 | Aarts ................ A61B 5/7275 600/485 |
| 2017/0027885 | A1 | 2/2017 | Ellers-Lenz et al. |
| 2017/0042739 | A1 | 2/2017 | O'Neill et al. |
| 2017/0189639 | A1* | 7/2017 | Mastrianni ............ A61B 5/378 |
| 2018/0018984 | A1* | 1/2018 | Dickins ............... G10L 21/0232 |
| 2018/0271710 | A1* | 9/2018 | Boesen ................ A61B 5/7203 |
| 2021/0106236 | A1* | 4/2021 | Tran ................. A61B 5/026 |
| 2021/0368282 | A1* | 11/2021 | Noda .................. H04R 25/75 |
| 2023/0056862 | A1 | 2/2023 | Song |

FOREIGN PATENT DOCUMENTS

| | | | |
|---|---|---|---|
| DK | 2485644 | T3 | 12/2016 |
| EP | 2485644 | B1 | 8/2016 |
| JP | 4249908 | B2 | 4/2009 |
| JP | 2019193795 | A | 11/2019 |
| JP | 6883716 | B2 | 6/2021 |
| KR | 101666474 | B1 * | 10/2016 |
| KR | 101744503 | B1 | 6/2017 |
| KR | 101754840 | B1 | 7/2017 |
| NZ | 580350 | A | 1/2012 |
| WO | WO-0242986 | A1 * | 5/2002 ......... G06F 19/3418 |
| WO | 03026349 | A1 | 3/2003 |
| WO | 2018007631 | A1 | 1/2018 |
| WO | 2020161460 | A1 | 8/2020 |
| WO | 2020188415 | A1 | 9/2020 |
| WO | 2021144964 | A1 | 7/2021 |
| WO | WO-2022047546 | A1 * | 3/2022 ......... A61B 5/0042 |

OTHER PUBLICATIONS

International Search Report and Written Opinion for International Application No. PCT/KR2022/007986; International Filing Date Jun. 7, 2022; Date of Mailing Sep. 21, 2022; 8 Pages.

European Search Report Issued In EP Application No. 22867502.1-1122, Mail Date Jul. 31, 2024, 10 Pages.

* cited by examiner

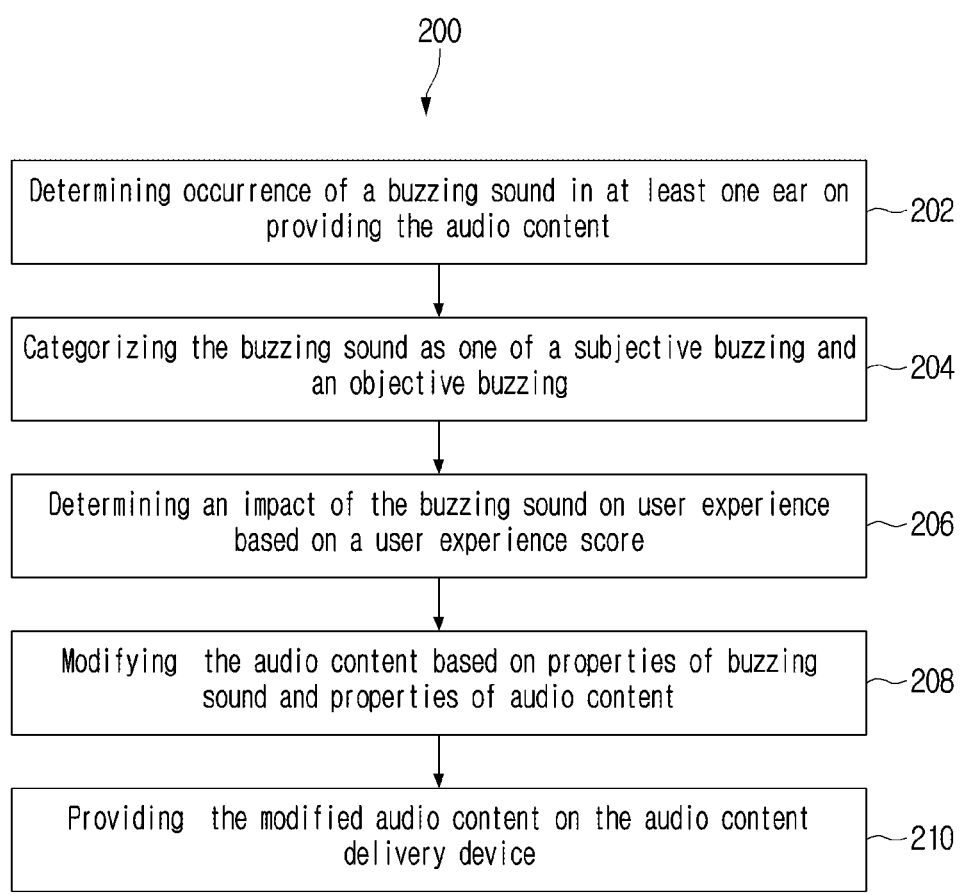

FIG. 5A

Multiple linear regression

Dependent variable (DV) 501
Independent variables (IVs) 502

$$y = b_0 + b_1^* x_1 + b_2^* x_2 + \ldots + b_n^* x_n$$

For adjusting coefficients to reduce error $$b_0 = Y - b_1 X_1 - b_2 X_2 - b_3 X_3 - b_4 X_4 - b_5 X_5 - b_6 X_6$$

$$b1 = \frac{(\sum X_1^2)(\sum X_1 Y) - (\sum X_1 X_2)(\sum X_2 Y) - (\sum X_1 X_3)(\sum X_3 Y) - (\sum X_1 X_4)(\sum X_4 Y) - (\sum X_1 X_5)(\sum X_5 Y) - (\sum X_1 X_6)(\sum X_6 Y)}{(\sum X_1^2)(\sum X_2^2)(\sum X_3^2)(\sum X_4^2)(\sum X_5^2)(\sum X_6^2) - (\sum X_1 X_2 X_3 X_4 X_5 X_6)}$$

$$b2 = \frac{(\sum X_2^2)(\sum X_2 Y) - (\sum X_2 X_1)(\sum X_1 Y) - (\sum X_2 X_3)(\sum X_3 Y) - (\sum X_2 X_4)(\sum X_4 Y) - (\sum X_2 X_5)(\sum X_5 Y) - (\sum X_2 X_6)(\sum X_6 Y)}{(\sum X_1^2)(\sum X_2^2)(\sum X_3^2)(\sum X_4^2)(\sum X_5^2)(\sum X_6^2) - (\sum X_1 X_2 X_3 X_4 X_5 X_6)}$$

$$b3 = \frac{(\sum X_3^2)(\sum X_3 Y) - (\sum X_3 X_1)(\sum X_1 Y) - (\sum X_3 X_2)(\sum X_2 Y) - (\sum X_3 X_4)(\sum X_4 Y) - (\sum X_3 X_5)(\sum X_5 Y) - (\sum X_3 X_6)(\sum X_6 Y)}{(\sum X_1^2)(\sum X_2^2)(\sum X_3^2)(\sum X_4^2)(\sum X_5^2)(\sum X_6^2) - (\sum X_1 X_2 X_3 X_4 X_5 X_6)}$$

$$b4 = \frac{(\sum X_4^2)(\sum X_4 Y) - (\sum X_4 X_1)(\sum X_1 Y) - (\sum X_4 X_2)(\sum X_2 Y) - (\sum X_4 X_3)(\sum X_3 Y) - (\sum X_4 X_5)(\sum X_5 Y) - (\sum X_4 X_6)(\sum X_6 Y)}{(\sum X_1^2)(\sum X_2^2)(\sum X_3^2)(\sum X_4^2)(\sum X_5^2)(\sum X_6^2) - (\sum X_1 X_2 X_3 X_4 X_5 X_6)}$$

$$b5 = \frac{(\sum X_5^2)(\sum X_5 Y) - (\sum X_5 X_1)(\sum X_1 Y) - (\sum X_5 X_2)(\sum X_2 Y) - (\sum X_5 X_3)(\sum X_3 Y) - (\sum X_5 X_4)(\sum X_4 Y) - (\sum X_5 X_6)(\sum X_6 Y)}{(\sum X_1^2)(\sum X_2^2)(\sum X_3^2)(\sum X_4^2)(\sum X_5^2)(\sum X_6^2) - (\sum X_1 X_2 X_3 X_4 X_5 X_6)}$$

$$b6 = \frac{(\sum X_6^2)(\sum X_6 Y) - (\sum X_6 X_1)(\sum X_1 Y) - (\sum X_6 X_2)(\sum X_2 Y) - (\sum X_6 X_3)(\sum X_3 Y) - (\sum X_6 X_4)(\sum X_4 Y) - (\sum X_6 X_5)(\sum X_5 Y)}{(\sum X_1^2)(\sum X_2^2)(\sum X_3^2)(\sum X_4^2)(\sum X_5^2)(\sum X_6^2) - (\sum X_1 X_2 X_3 X_4 X_5 X_6)}$$

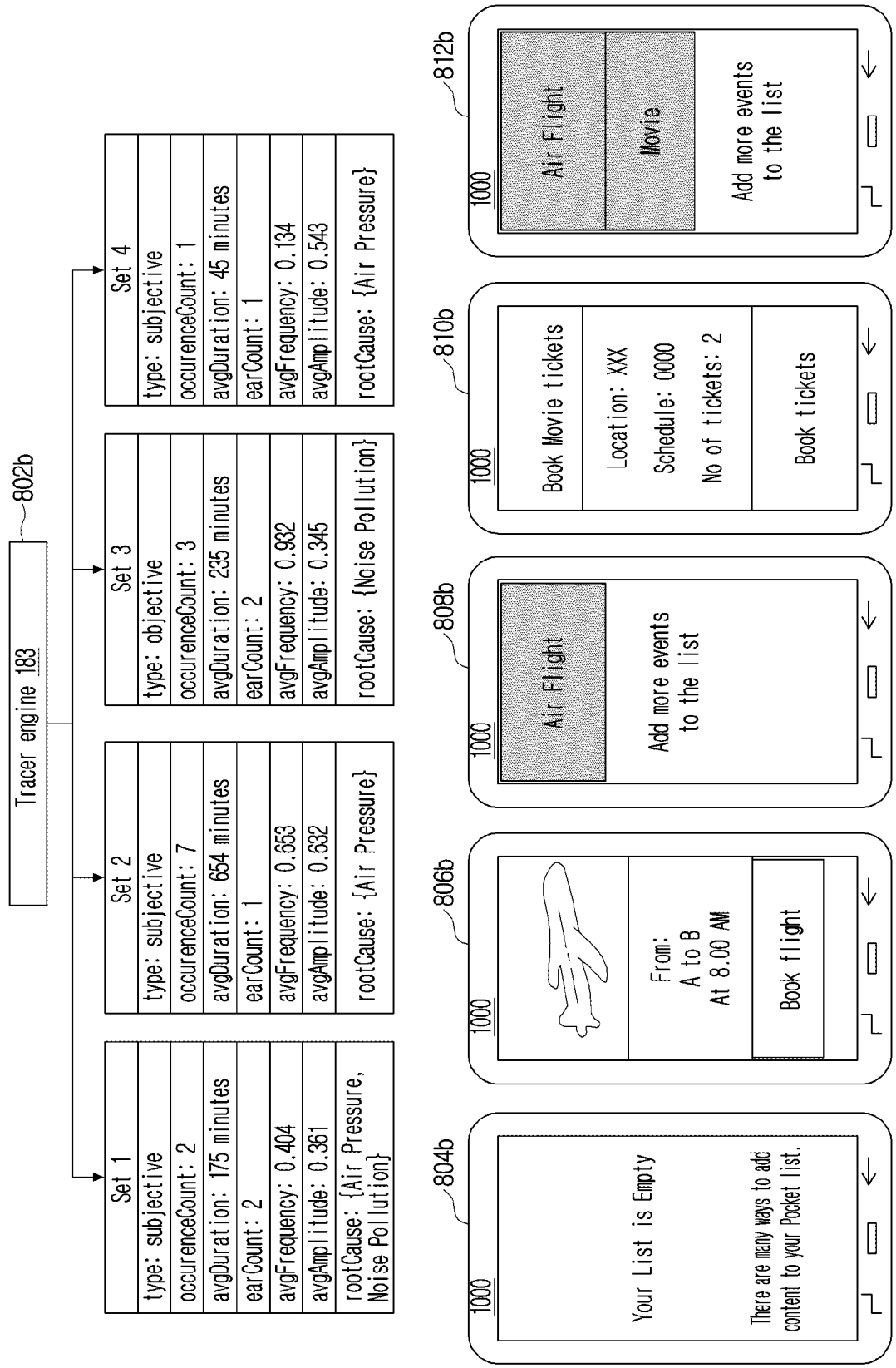

MANAGING AUDIO CONTENT DELIVERY

TECHNICAL FIELD

The present disclosure relates to audio signal processing and, more specifically, to a method and audio content delivery device for managing audio content delivery to a user experiencing buzzing sound.

BACKGROUND ART

Generally, tinnitus is the perception of sound even in the absence of an external source of such sound. Tinnitus can be perceived in one or both ears, in the head, or outside the head. Tinnitus is usually described as a ringing noise but can also be in other forms such as hissing, buzzing, or roaring sounds. Tinnitus can be intermittent, or continuous. Tinnitus can cause long-term hearing loss, insomnia, depression, and brain restlessness, among other effects.

Tinnitus is not a disease but a symptom resulting from a range of possible underlying causes, including, for example, ear infections, foreign objects, ear-wax, external noise pollution, air pressure, age, and the like. Further, detecting the tinnitus requires medical tests such as audiogram tests, tympanogram tests, etc. In addition, Electroencephalogram (EEG) signals are analyzed for detecting tinnitus using a computer-aided technique. The existing techniques involve tedious tasks and a requirement for medical assistance to detect the tinnitus.

Upon detecting the tinnitus, the existing solutions provide temporary relief for the user by using external sound devices, for example, masking instruments, olive pro hearing aid, and the like. However, the existing solutions are non-user friendly, and the external sound devices involve a higher cost making them non-affordable to the user.

In view of the disadvantages mentioned above, there is a need to detect an onset of tinnitus in real-time or predict the occurrence of the tinnitus for the user and provide (or recommend) an audio content to reduce the effect of tinnitus and/or avert the occurrence of tinnitus.

Thus, it is desired to at least provide a mechanism for autofocus that is devoid of the above issues.

DISCLOSURE OF INVENTION

Technical Problem

One or more embodiments of technical solutions described herein provide audio content delivery for managing audio content delivery to a user experiencing a buzzing sound. A method for delivering the audio includes determining the impact of the buzzing sound on the user and effectively modifying the audio content to be delivered based on the impact of the buzzing sound on the user. The audio content, in some embodiments, is modified by using a white noise which reduces the impact of the buzzing sound on the user. Also, specific pre-set properties of the audio content can be modified to enhance the user experience.

Alternatively, or in addition, embodiments of technical solutions described herein, determine future events which could cause the buzzing sound and use user-history to manage (i.e., reduce the impact of) the buzzing sound intelligently and specific to the user. Accordingly, embodiments of technical solutions described herein addresses the technical challenges associated with the buzzing sound encountered by the user. Embodiments of the technical solutions described herein mitigate the effects of the buzzing in real-time. Further, embodiments of the technical solutions described herein improve computing technology by efficiently, mitigating the buzzing sound. It should be noted that the buzzing sound can cause short-term as well as long-term impacts on the user's health. Technical solutions described herein accordingly provide improvements to computing technology, particularly, audio-processing devices (e.g., headphones, earphones, hearing aids, etc.). further, technical solutions described herein provide practical applications in the field of audio-processing, as well as tinnitus management.

Solution to Problem

Embodiments of technical solutions described herein include a method to deliver audio content by an audio content delivery device. The method includes determining, by the audio content delivery device, occurrence of a buzzing sound in at least one ear on providing the audio content. Further, the method includes categorizing, by the audio content delivery device, the buzzing sound as one of a subjective buzzing and an objective buzzing. The method also includes determining, by the audio content delivery device, an impact of the buzzing sound on user experience based on a user experience score. Further, the method includes modifying, by the audio content delivery device, the audio content based on properties of buzzing sound and properties of audio content. Further, the method includes providing, by the audio content delivery device, the modified audio content on the audio content delivery device.

In an embodiment, determining, by the audio content delivery device, the occurrence of the buzzing sound in the at least one ear on providing the audio content includes receiving, by the audio content delivery device, the audio content provided in the at least one ear and reducing, by the audio content delivery device, a noise present in the audio content. The method also includes removing, by the audio content delivery device, non-essential portions of the audio content and extracting, by the audio content delivery device, a plurality of features of the audio content. Further, the method includes obtaining, by the audio content delivery device, normalized values of each of the plurality of features by scaling the extracted plurality of features of the audio content. The method further includes providing, by the audio content delivery device, the normalized values of each of the plurality of features as an input to a pre-trained first Artificial Intelligence (AI) model. The method includes determining, by the audio content delivery device, the occurrence of the buzzing sound in the at least one ear based on an output of the pre-trained first AI model.

In an embodiment, the buzzing sound is categorized as one of the subjective buzzing sound and the objective buzzing sound based on the audio content delivery device and a trained model.

In an embodiment, the method also includes determining, by the audio content delivery device, that the buzzing sound is categorized as the objective buzzing sound. Further, the method includes determining, by the audio content delivery device, a heart rate and blood pressure of a user, and classifying the objective buzzing sound as one of pulsatile buzzing and non-pulsatile buzzing based on the heart rate and the blood pressure of the user.

In an embodiment, the method also includes determining, by the audio content delivery device, a plurality of properties of the categorized buzzing sound. The method further includes storing, by the audio content delivery device, the plurality of properties of the categorized buzzing sound and user context.

In an embodiment, determining, by the audio content delivery device, the impact of the buzzing sound on the user experience based on the user experience score includes determining, by the audio content delivery device, a plurality of parameters associated with the buzzing sound and the user. The plurality of parameters associated with the buzzing sound and the user comprises an age of the user, an ear type of the user, emotional index of the user, a duration of the buzzing sound, an amplitude of the buzzing sound and a metric of noise pollution. The method also includes determining, by the audio content delivery device, an impact score based on the plurality of parameters associated with the buzzing sound and the user. The method further includes determining, by the audio content delivery device, the user experience score using the impact score. The method also includes determining, by the audio content delivery device, whether the user experience score is below a user experience threshold. The method further includes determining, by the audio content delivery device, that the impact of the buzzing sound on the user experience is high and the audio content needs to be modified, in response to determining that the experience score is below a user experience threshold. It is determined that the impact of the buzzing sound on the user experience is low and the audio content need not be modified, in response to determining that the experience score is above the user experience threshold.

In an embodiment, modifying, by the audio content delivery device, the audio content based on properties of the buzzing sound and the properties of audio content includes determining, by the audio content delivery device, the impact of the buzzing sound on the user experience is high and the audio content needs to be modified. The method further includes modifying, by the audio content delivery device, by masking a white noise with the buzzing sound. The white noise is generated based on the properties of the buzzing sound and the properties of audio content, and applying at least one modified pre-set to change at least one property of the plurality of properties of the audio content.

In an embodiment, the method includes determining, by the audio content delivery device, the at least one modified pre-set is applied to the audio content. The method also includes determining, by the audio content delivery device, a resemblance between the at least one modified pre-set and at least one new audio content of a plurality of audio contents in a playlist of the user; and reordering, by the audio content delivery device, priority of the at least one new audio content in the playlist of the user.

In an embodiment, providing, by the audio content delivery device, the modified audio content on the audio content delivery device to the user includes determining, by the audio content delivery device, at least one new audio content of a plurality of audio contents in a playlist of the user based on the user experience score and the properties of the audio content being played; and providing, by the audio content delivery device, a recommendation of the at least one new audio content to the user.

In an embodiment, the method also includes detecting, by the audio content delivery device, at least one event which creates the buzzing sound. The method further includes providing, by the audio content delivery device, a suggestion to the user to put on the audio content delivery device. The method further includes generating, by the audio content delivery device, a white noise in advance based on user history for averting the buzzing sound.

In an embodiment, the method also includes detecting, by the audio content delivery device, at least one future event of the user. The method further includes determining, by the audio content delivery device, the buzzing sound associated with the at least one future event and the properties of the buzzing sound associated with the at least one future event based on a user history The method further includes providing, by the audio content delivery device, a notification on an electronic device of the user for averting the buzzing sound.

Accordingly, embodiments herein facilitate an audio content delivery device for managing audio content delivery. The audio content delivery device includes a memory, a processor, a communicator and an audio content management controller. The audio content management controller is configured to determine occurrence of a buzzing sound in at least one ear on providing the audio content and categorize the buzzing sound as one of a subjective buzzing and an objective buzzing. Further, the audio content management controller is also configured to determine an impact of the buzzing sound on user experience based on a user experience score, modify the audio content based on properties of buzzing sound and properties of audio content, and provide the modified audio content on the audio content delivery device.

These and other aspects of the technical solutions herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein, and the embodiments herein include all such modifications.

BRIEF DESCRIPTION OF DRAWINGS

This invention is illustrated in the accompanying drawings, throughout which like reference letters indicate corresponding parts in the various figures. The embodiments herein will be better understood from the following description with reference to the drawings, in which:

FIG. 2 is a flow diagram illustrating a method for managing the audio content delivery by the audio content delivery device, according to an embodiment as disclosed herein;

FIG. 5A illustrates a multiple regression model used to determine user experience score by a user experience management controller, according to an embodiment as disclosed herein;

FIG. 8B is an example of event detection and management of the audio content delivery by the audio content delivery device, according to the embodiments as disclosed herein.

MODE FOR THE INVENTION

Figure 1:
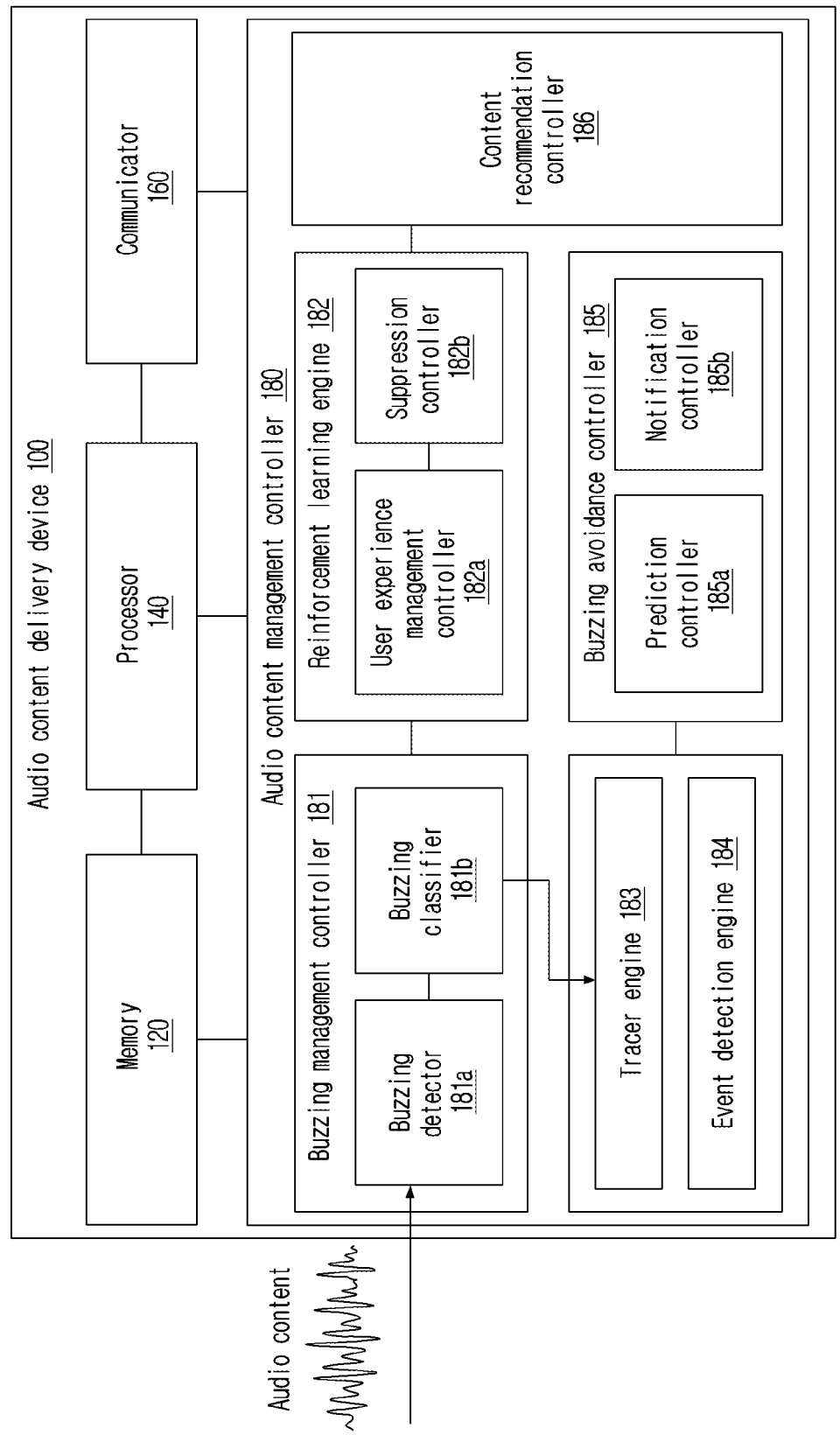
FIG. 1 illustrates a block diagram of an audio content delivery device for managing an audio content delivery to a user, according to an embodiment as disclosed herein.

Embodiments of technical solutions described herein include a method to deliver audio content by an audio content delivery device. The method includes determining, by the audio content delivery device, occurrence of a buzzing sound in at least one ear on providing the audio content. Further, the method includes categorizing, by the audio content delivery device, the buzzing sound as one of a subjective buzzing and an objective buzzing. The method also includes determining, by the audio content delivery device, an impact of the buzzing sound on user experience based on a user experience score. Further, the method includes modifying, by the audio content delivery device, the audio content based on properties of buzzing sound and properties of audio content. Further, the method includes providing, by the audio content delivery device, the modified audio content on the audio content delivery device.

As is traditional in the field, embodiments may be described and illustrated in terms of blocks which carry out a described function or functions. These blocks, which may be referred to herein as units or modules or the like, are physically implemented by analog or digital circuits such as logic gates, integrated circuits, microprocessors, microcontrollers, memory circuits, passive electronic components, active electronic components, optical components, hardwired circuits, or the like, and may optionally be driven by firmware. The circuits may, for example, be embodied in one or more semiconductor chips, or on substrate supports such as printed circuit boards and the like. The circuits constituting a block may be implemented by dedicated hardware, or by a processor (e.g., one or more programmed microprocessors and associated circuitry), or by a combination of dedicated hardware to perform some functions of the block and a processor to perform other functions of the block. Each block of the embodiments may be physically separated into two or more interacting and discrete blocks without departing from the scope of the invention. Likewise, the blocks of the embodiments may be physically combined into more complex blocks without departing from the scope of the invention.

The accompanying drawings are used to help understand various technical features and it should be understood that the embodiments presented herein are not limited by the accompanying drawings. As such, the present disclosure should be construed to extend to any alterations, equivalents and substitutes in addition to those which are particularly set out in the accompanying drawings. Although the terms first, second, etc., may be used herein to describe various elements, these elements should not be limited by these terms. These terms are generally only used to distinguish one element from another.

Embodiments herein facilitate a method for managing audio content delivery by an audio content delivery device. The method includes determining, by the audio content delivery device, occurrence of a buzzing sound in at least one ear on providing the audio content and categorizing, by the audio content delivery device, the buzzing sound as one of a subjective buzzing and an objective buzzing based on the audio content delivery device. The method also includes determining, by the audio content delivery device, an impact of the buzzing sound on user experience based on a user experience score and modifying, by the audio content delivery device, the audio content based on properties of buzzing sound and properties of audio content. The method further includes providing, by the audio content delivery device, the modified audio content on the audio content delivery device.

Embodiments herein facilitate an audio content delivery device for managing audio content delivery. The audio content delivery device includes a memory, a processor, a communicator and an audio content management controller. The audio content management controller is configured to determine occurrence of a buzzing sound in at least one ear on providing the audio content and categorize the buzzing sound as one of a subjective buzzing and an objective buzzing based on the audio content delivery device. Further, the audio content management controller is also configured to determine an impact of the buzzing sound on user experience based on a user experience score, modify the audio content based on properties of buzzing sound and properties of audio content, and provide the modified audio content on the audio content delivery device.

Conventional methods and systems identify the buzzing sound manually by frequency matching using external device and user input. Therefore, the conventional methods and systems require external input, output to find attributes for suppressing the Buzzing effect.

Conventional methods and systems, do not consider external parameters such as for example pressure change and noise pollution while addressing the buzzing sound. Also, there are no provisions of detecting and identifying ear wax.

Unlike conventional methods and systems, the technical solutions herein do not require external devices for identifying attributes for suppressing buzzing effect and to manage the buzzing sound. The audio content delivery device which includes two external microphones (mics) and a VPU embedded are only used for efficiently managing the buzzing sound and enhancing user experience.

Unlike conventional methods and systems, the technical solutions herein not just classify the detected buzzing sound, but also identify a possible root cause of the buzzing sound and recommend users in advance if same or similar event repeats.

Unlike the conventional methods and systems, the technical solutions herein take into account user's health parameter (e.g., blood pressure, heart-rate, etc.) and external parameters (e.g., air-pressure change, noise pollution, etc.) while calculating buzzing magnitude and its effect on user experience.

Ear wax build-up left untreated can cause permanent damage, resulting in chronic buzzing. The ear wax is an obstruction in middle ear that can increase pressure in the inner ear, causing the buzzing. Additionally, the ear wax may absorb some amplitude of sound and also reflect some of the sound. Unlike the conventional methods and systems, the technical solutions herein identify ear wax and can determine buzzing and its effects even in the presence of ear wax.

Unlike conventional methods and systems, the technical solutions herein automatically identify a buzzing that a user is experiencing without user input. Traditionally, a user input is required to detect if the user is experiencing a buzzing sound or not. Technical solutions herein not only automatically detect the occurrence of buzzing, but also facilitate classifying the buzzing into different types of buzzing like objective/subjective/objective pulsatile using inbuilt sensors in the audio content delivery device, such as ear buds, earphones, head phones, etc.

Technical solutions herein facilitate detection and identification of the buzzing sound before it becomes a chronic problem and provide measures to overcome the buzzing. Technical solutions herein further facilitate an enhanced user experience by modifying sound properties and generating white noise. Technical solutions herein facilitate the several advantages and improvements described herein without any external device such as for frequency matching or white noise generation.

FIG. 1 illustrates a block diagram of an audio content delivery device (100) for managing an audio content delivery to a user, according to an embodiment as disclosed herein. The audio content delivery device (100) can be, but not limited to a wired earphone, a wireless earphone, ear buds, an over ear audio device, etc.

In an embodiment, the audio content delivery device (100) includes a memory (120), a processor (140), a communicator (160) and an audio content management controller (180).

The memory (120) is configured to store plurality of user profiles and corresponding buzzing sounds detected. The memory (120) also stores user experience scores associated with specific buzzing sound, preferable pre-set for a specific user, etc. The memory (120) is also configured to store instructions to be executed by the processor (140). The memory (120) may include non-volatile storage elements. Examples of such non-volatile storage elements may include magnetic hard discs, optical discs, floppy discs, flash memories, or forms of electrically programmable memories (EPROM) or electrically erasable and programmable (EEPROM) memories. In addition, the memory (120) may, in some examples, be considered a non-transitory storage medium. The term "non-transitory" may indicate that the storage medium is not embodied in a carrier wave or a propagated signal. However, the term "non-transitory" should not be interpreted that the memory (120) is non-movable. In some examples, the memory (120) can be configured to store larger amounts of information. In certain examples, a non-transitory storage medium may store data that can, over time, change (e.g., in Random Access Memory (RAM) or cache).

The processor (140) communicates with the memory (120), the communicator (160) and the audio content management controller (180). The processor (140) is configured to execute instructions stored in the memory (120) and to perform various processes. The processor may include one or a plurality of processors, may be a general purpose processor, such as a central processing unit (CPU), an application processor (AP), or the like, a graphics-only processing unit such as a graphics processing unit (GPU), a visual processing unit (VPU), and/or an Artificial intelligence (AI) dedicated processor such as a neural processing unit (NPU).

The communicator (160) includes an electronic circuit specific to a standard that enables wired or wireless communication. The communicator (160) is configured to communicate internally between internal hardware components of the audio content delivery device (100) and with external devices via one or more networks.

In an embodiment, the audio content management controller (180) includes a buzzing management controller (181), a reinforcement learning engine (182), a tracer engine (183), an event detection engine (184), buzzing avoidance controller (185) and a content recommendation controller (186). The audio content management controller (180) is implemented by processing circuitry such as logic gates, integrated circuits, microprocessors, microcontrollers, memory circuits, passive electronic components, active electronic components, optical components, hardwired circuits, or the like, and may optionally be driven by firmware. The circuits may, for example, be embodied in one or more semiconductors.

The buzzing management controller (181) includes a buzzing detector (181a) and a buzzing classifier (181b). In an embodiment, the buzzing detector (181a) is configured to receive the audio content provided in the at least one ear and reduce a noise present in the audio content. The buzzing detector (181a) is also configured to remove non-essential portions of the audio content and extract a plurality of features of the audio content. Further, the buzzing detector (181a) is configured to obtain normalized values of each of the plurality of features by scaling the extracted plurality of features of the audio content, provide the normalized values of each of the plurality of features as an input to a pre-trained first Artificial Intelligence (AI) model and determine the occurrence of the buzzing sound in the at least one ear based on an output of the pre-trained first AI model.

In an embodiment, the buzzing classifier (181b) is configured to categorize the buzzing sound as one of a subjective buzzing and an objective buzzing based on the audio content delivery device (100). Further, the buzzing classifier (181b) is also configured to determine that the buzzing sound is categorized as the objective buzzing sound and determine a heart rate and blood pressure of a user. Further, the buzzing classifier (181b) is configured to classify the objective buzzing sound as one of pulsatile buzzing and non-pulsatile buzzing based on the heart rate and the blood pressure of the user. The buzzing classifier (181b) is configured to determine a plurality of properties of the categorized buzzing sound and send the plurality of properties of the categorized buzzing sound and user context to the tracer engine (183).

In an embodiment, the tracer engine (183) is configured to store the plurality of properties of the categorized buzzing sound and user context sent by the buzzing classifier (181b). The tracer engine (183) is a json file which stored mean frequency, mean amplitude, etc., to map it with root cause and avoid future incidents of the buzzing sound.

The reinforcement learning engine (182) includes a user experience management controller (182a) and a suppression controller (182b). In an embodiment, the user experience management controller (182a) is configured to determine a plurality of parameters associated with the buzzing sound and the user, and determine an impact score based on the plurality of parameters associated with the buzzing sound and the user. The plurality of parameters associated with the buzzing sound and the user include but are not limited to: an age of the user, an ear type of the user, emotional index of the user, duration of the buzzing sound, amplitude of the buzzing sound and noise pollution. Further, the user experience management controller (182a) is configured to determine the user experience score using the impact score and to determine whether the user experience score is below a user experience threshold. Further, the user experience management controller (182a) determines that the impact of the buzzing sound on the user experience is high and the audio content needs to be modified, in response to determining that the experience score is below the user experience threshold, and the impact of the buzzing sound on the user experience is low and the audio content need not be modified, in response to determining that the experience score is above the user experience threshold.

In an embodiment, the suppression engine (182b) is configured to determine the impact of the buzzing sound on the user experience is high and the audio content needs to be modified. Further, the suppression engine (182b) is configured to modify by masking the buzzing sound with a white noise and apply a modified pre-set to change at least one property of the plurality of properties of the audio content. The white noise is generated based on the properties of the buzzing sound and the properties of audio content.

In an embodiment, the content recommendation controller (186) is configured to determine a resemblance between the at least one modified pre-set and at least one new audio content of a plurality of audio contents in a playlist of the user and reorder priority of the at least one new audio content in the playlist of the user. The at least one modified pre-set may be soothing to the user and hence the reordering/updating of the playlist not only addresses the buzzing sound but also provides relief to the user.

In another embodiment, the content recommendation controller (186) is configured to determine at least one new audio content of a plurality of audio contents in a playlist of the user based on the user experience score and the properties of the audio content being played and provide a recommendation of the at least one new audio content to the user.

In an embodiment, the event detection engine (184) is configured to detect at least one event which creates the buzzing sound. The event can be, for example, a present event or a future event. The future event may be detected based on user activity on an electronic device associated with the audio content delivery device (100). For example, a user books air travel tickets for travel a month later. The event detection engine (184) detects the event and stores the same with corresponding date.

The buzzing avoidance controller (185) includes prediction controller (185a) and a notification controller (185b). In an embodiment, the prediction controller (185a) is configured to indicate the notification controller (185b) to generate a suggestion to the user to put on the audio content delivery device (100) based on the event detected by the event detection engine (184). The prediction controller (185a) is configured to generate a white noise in advance based on user history for averting the buzzing sound.

In another embodiment, the prediction controller (185a) is configured to determine the buzzing sound associated with the at least one future event and the properties of the buzzing sound associated with the at least one future event based on a user history and indicate to the notification controller (185b) to send a notification to the user.

In an embodiment, the notification controller (185b) is configured to provide the suggestion to the user to put on the audio content delivery device (100) based on the event detected by the event detection engine (184). The notification controller (185b) is configured to provide the notification on an electronic device of the user for averting the buzzing sound. The notification may be, for example, a pop-up message, an audio command, a video with instructions, etc. and may be determined based on the user preference.

At least one of the plurality of modules/components of the audio content management controller (180) may be implemented through an AI model. A function associated with the AI model may be performed through memory (120) and the processor (140). The one or more processors control the processing of the input data in accordance with a predefined operating rule or the AI model stored in the non-volatile memory and the volatile memory. The predefined operating rule or artificial intelligence model is provided through training or learning.

Here, being provided through training or learning indicates that a predefined operating rule or AI model is trained using training data (training phase) to provide a desired characteristic when input with unknown data (inference phase). The learning/training may be performed in the device in which the AI model is being used, and/or in a server/system separate from the device in which the AI model is being used.

The AI model may include a plurality of neural network layers. Each layer has a plurality of weight values and performs a layer operation through calculation of a previous layer and an operation of a plurality of weights. Examples of neural networks include, but are not limited to, convolutional neural network (CNN), deep neural network (DNN), recurrent neural network (RNN), restricted Boltzmann Machine (RBM), deep belief network (DBN), bidirectional recurrent deep neural network (BRDNN), generative adversarial networks (GAN), and deep Q-networks.

The learning/training process is a method for training a predetermined target device (for example, a robot) using a plurality of learning data to cause, allow, or control the target device to make a determination or prediction. Examples of learning processes include, but are not limited to, supervised learning, unsupervised learning, semi-supervised learning, or reinforcement learning.

Although FIG. 1 shows various hardware components of the audio content delivery device (100) but it is to be understood that other embodiments are not limited thereon. In other embodiments, the audio content delivery device (100) may include less or more number of components. Further, the labels or names of the components are used only for illustrative purpose and does not limit the scope of the invention. One or more components can be combined together to perform same or substantially similar function to manage the audio content delivery while the buzzing sound is detected.

FIG. 2 is a flow diagram illustrating a method (200) for managing the audio content delivery by the audio content delivery device (100), according to an embodiment as disclosed herein.

Referring to the FIG. 2, at step 202 the method includes the audio content delivery device (100) determining the occurrence of the buzzing sound in at least one of the user's ear upon/during providing the audio content. For example, in the audio content delivery device (100) described in the FIG. 1, the audio content management controller (180) is configured to determine the occurrence of the buzzing sound in the ear when providing the audio content.

At step 204, the method includes the audio content delivery device (100) categorizing the buzzing sound as the subjective buzzing or the objective buzzing. For example, in the audio content delivery device (100) described in the FIG. 1, the audio content management controller (180) is configured to categorize the buzzing sound as the subjective buzzing or the objective buzzing.

At step 206, the method includes the audio content delivery device (100) determining the impact of the buzzing sound on the user experience based on the user experience score. For example, in the audio content delivery device (100) described in the FIG. 1, the audio content management controller (180) is configured to determine the impact of the buzzing sound on the user experience based on the user experience score.

At step 208, the method includes the audio content delivery device (100) modifying the audio content based on the properties of buzzing sound and the properties of the audio content. For example, in the audio content delivery device (100) described in the FIG. 1, the audio content management controller (180) is configured to modify the audio content based on the properties of buzzing sound and the properties of the audio content.

At step 210, the method includes the audio content delivery device (100) providing the modified the audio content on the audio content delivery device (100). For example, in the audio content delivery device (100) described in the FIG. 1, the audio content management controller (180) is configured to provide the modified the audio content on the audio content delivery device (100).

The various actions, acts, blocks, steps, or the like in the flow diagram (200) may be performed in the order presented, in a different order or simultaneously. Further, in some embodiments, some of the actions, acts, blocks, steps, or the like may be omitted, added, modified, skipped, or the like without departing from the scope of the invention.

Figure 3A:
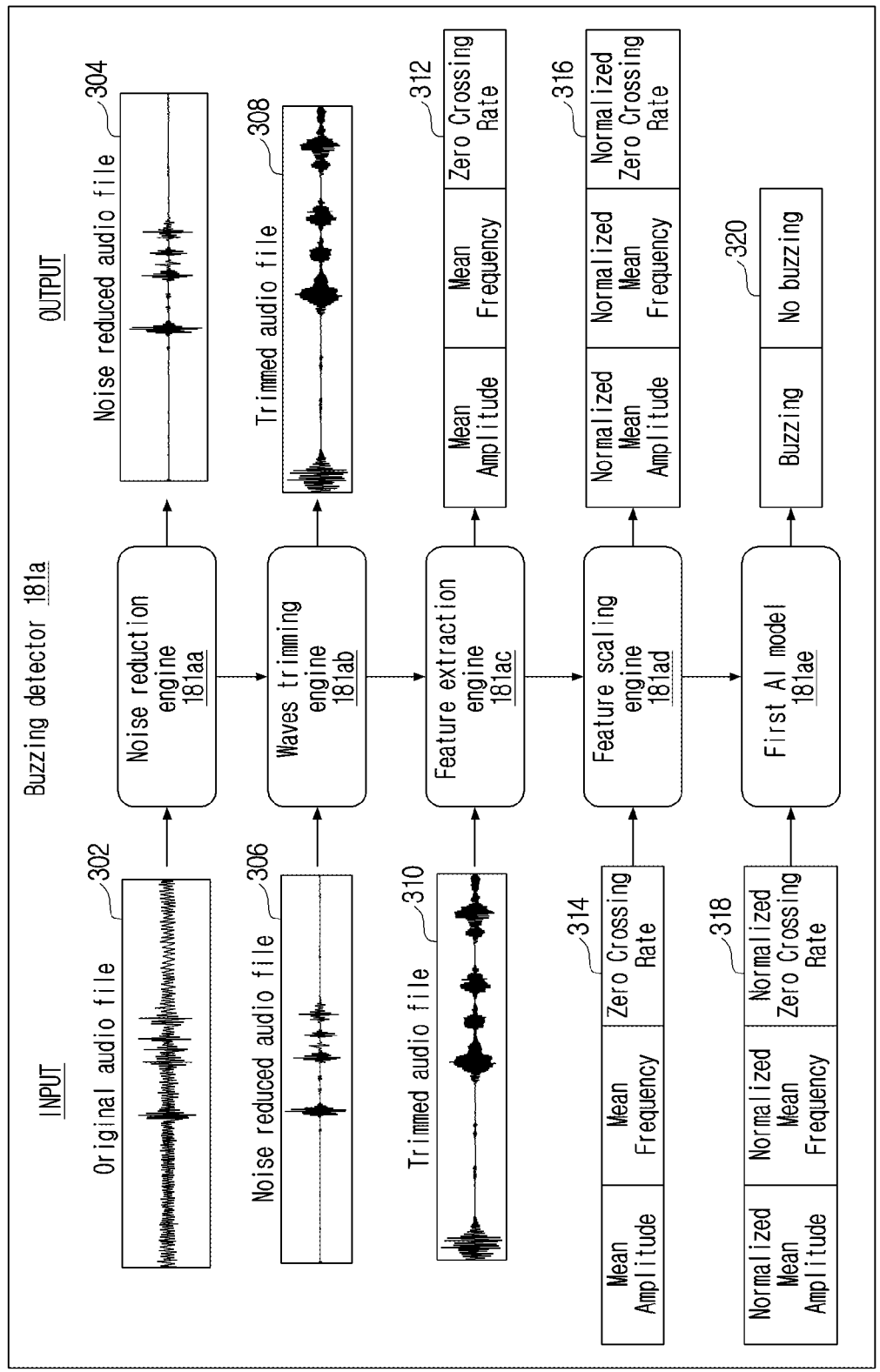
FIG. 3A illustrates functioning of a buzzing detector, according to an embodiment as disclosed herein.

FIG. 3A illustrates functioning of the buzzing detector (181a), according to an embodiment as disclosed herein. Referring to the FIG. 3A, the buzzing detector (181a) includes noise reduction engine (181aa), a waves trimming engine (181ab), a feature extraction engine (181ac), a feature scaling engine (181ad) and a first AI model (181ae).

At step 302 the original audio file is provided as input to the noise reduction engine (181aa) to receive noise reduced audio file as output at step 304. One or more embodiments use spectral gating algorithm to reduce the noise in the original audio file and librosa library for analyzing audio.

At step 306, the noise reduced audio file is provided as input to the waves trimming engine (181ab) to receive the trimmed audio file as output at step 308. The Librosa library is used in one or more embodiments to analyze the audio (e.g., speech, music, and combination thereof) and to trim unwanted portions of the audio. The audio can be provided as an audio file, streaming audio, or in any other digital/electronic format that can be processed by the audio content delivery device 100.

At step 310, the trimmed audio is provided as input to the feature extraction engine (181ac) to identify multiple features of the trimmed audio as output at step 312. The multiple features of the trimmed audio include mean amplitude, mean frequency, and zero crossing rate of the trimmed audio. At step 314, the multiple features of the trimmed audio are provided as input to the feature scaling engine (181ad) to generate a normalized version of the multiple features of the trimmed audio as output at step 316. At step 318, the multiple features of the trimmed audio are provided as input to the first AI model (181ae) to provide an output indicating whether the buzzing sound is detected or not, at step 320.

Figure 3B:
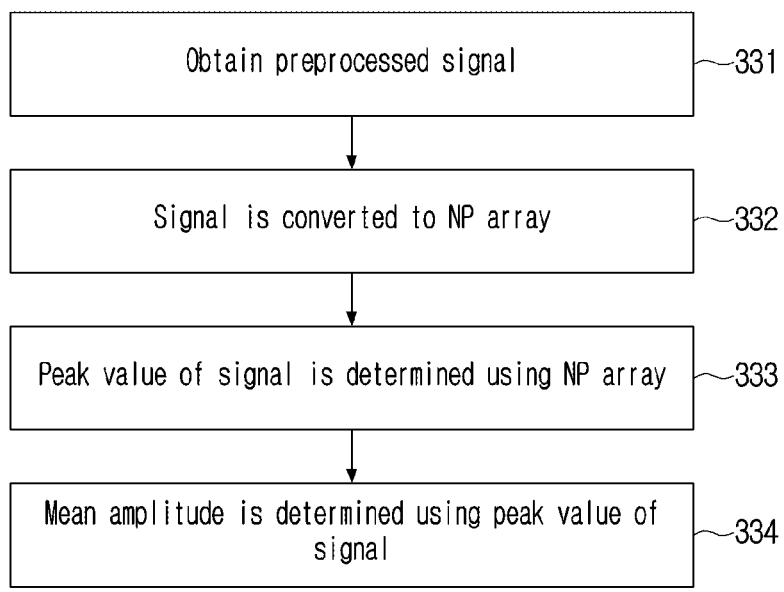
FIG. 3B is a flow chart for a method for determining a mean amplitude of a trimmed audio file by a feature extraction engine, according to an embodiment as disclosed herein.

FIG. 3B is a flow chart for the method for determining the mean amplitude of the trimmed audio by the feature extraction engine (181ac), according to one or more embodiments herein.

Referring to the FIG. 3B, at step 331, the pre-processed trimmed audio is obtained by the feature extraction engine (181ac). At step 332, the pre-processed trimmed audio is converted into a numpy (NP) array. At step 333, peak values of the signal i.e., both upper peak and lower peak are determined. To get the loudness of the buzzing sound a Numpy library is used for converting way file in an array to find the mean amplitude (step 334). It should be noted that different libraries and audio formats from those described herein can be used in other embodiments.

Figure 3C:
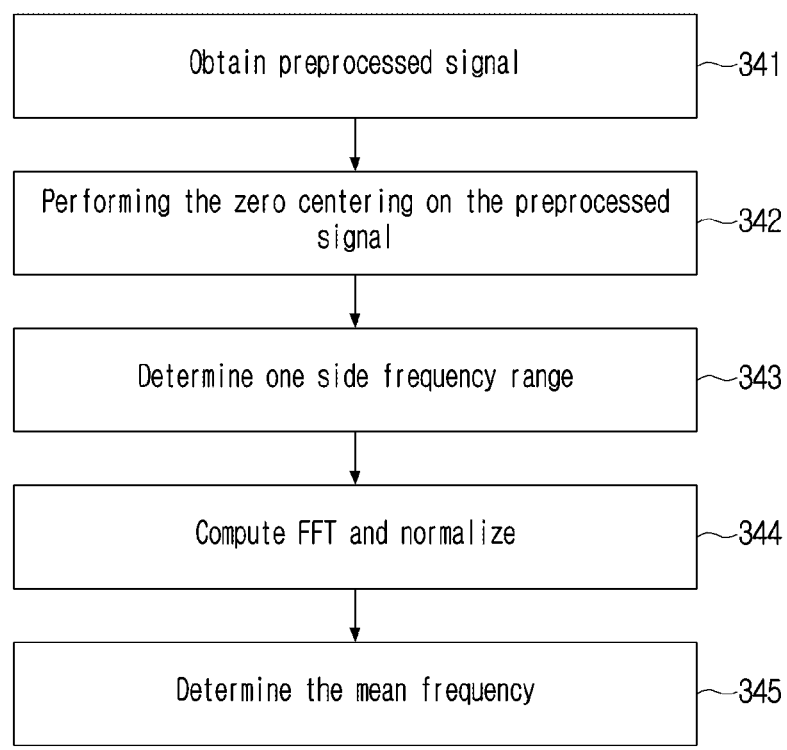
FIG. 3C is a flow chart for a method for determining a mean frequency of the trimmed audio file by the feature extraction engine, according to an embodiment as disclosed herein.

FIG. 3C is a flow chart for the method for determining the mean frequency of the trimmed audio file by the feature extraction engine (181ac), according to an embodiment as disclosed herein.

Referring to the FIG. 3C, at step 341, the pre-processed trimmed audio is obtained by the feature extraction engine (181ac). At step 342, a zero centring is performed on the pre-processed signal. At step 343, a one side frequency range is determined. At step 344, a fast Fourier transform (FFT) is performed on the one side frequency data obtained. At step 345, the mean frequency is obtained. Therefore, a pitch of the buzzing sound is obtained. The Numpy library is used for converting way file in an array to find mean frequency in one or more embodiments; however, in other embodiments, other tools and/or libraries can also be used.

Figure 3D:
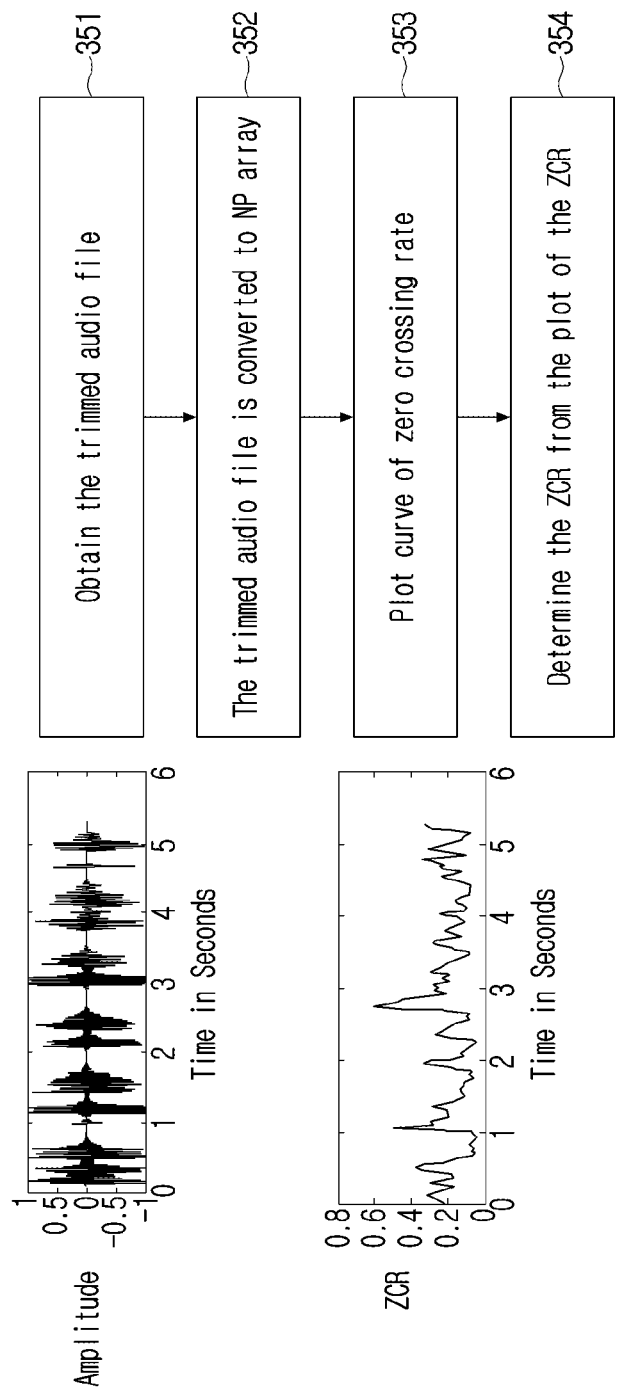
FIG. 3D is a flow chart for a method for determining a zero crossing rate of the trimmed audio file by the feature extraction engine, according to an embodiment as disclosed herein.

FIG. 3D is a flow chart for the method for determining the zero crossing rate of the trimmed audio by the feature extraction engine (181ac), according to an embodiment as disclosed herein.

Referring to the FIG. 3D, at step 351, the pre-processed trimmed audio is obtained by the feature extraction engine (181ac). At step 352, the pre-processed trimmed audio is converted into a numpy (NP) array. At step 353, a curve of zero crossing rate (ZCR) is plotted with respect to time. At step 354, the ZCR value is obtained from the ZCR plot. A high ZCR value (above a predetermined threshold) usually indicates continuous buzzing sound. The Librosa library is used to find the ZCR of input signal in one or more embodiments; however, other libraries/tools can be used in other embodiments.

Figure 3E:
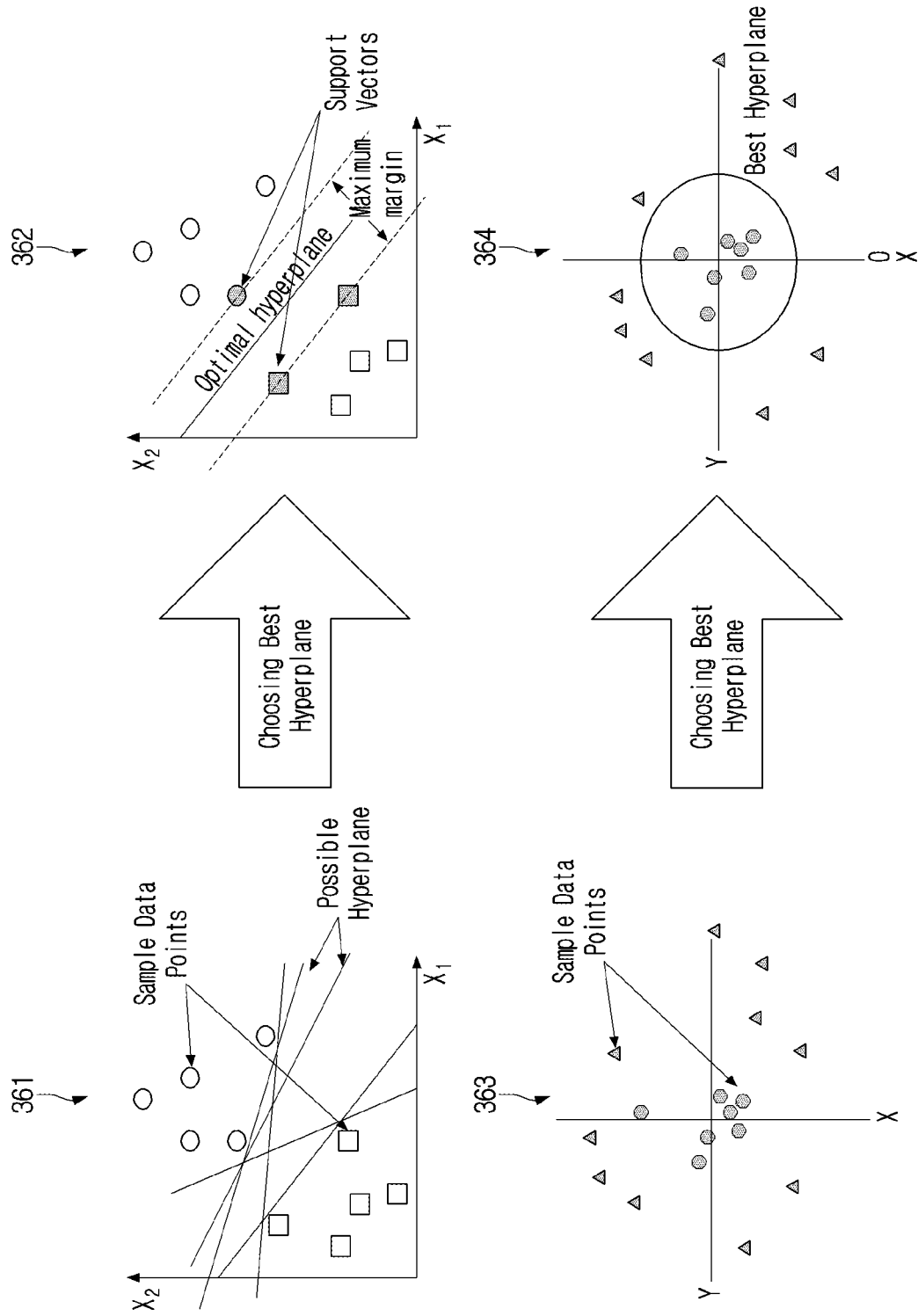
FIG. 3E illustrates a method for determining a maximum marginal hyperplane by a first AI model, according to an embodiment as disclosed herein.

FIG. 3E illustrates a method for determining a maximum marginal hyperplane by the first AI model (181ae), according to an embodiment as disclosed herein.

Referring to the FIG. 3E, the first AI model (181ae) uses support vector machines (SVM) a supervised machine learning (ML) technique that offers high accuracy to determine whether the buzzing sound is present or not. The SVM finds an optimal hyperplane which helps in determining the normalized plurality of parameters in an iterative manner, which minimizes error. At step 361, consider that the support vectors are linear separable data, which are closest to the hyperplane. These points will define the separating line better by calculating margins. These points are more relevant to the construction of the first AI model (181ae). The SVM searches for a maximum marginal hyperplane (MMH) between the support vectors that best divides the dataset into classes.

The hyperplanes are decision boundaries that help classify the data points. The data points falling on either side of the hyperplane can be attributed to different classes. The support vectors are data points that are closer to the hyperplane and influence the position and orientation of the hyperplane. Using these support vectors, we maximize the margin of the classifier. The maximum margin using support vectors we have to maximize the margin between two points i.e. the maximum distance between data points of both classes.

The first AI model (181ae) generates the hyperplanes which segregates the classes in the best way and selects the right hyperplane with the maximum segregation from the either nearest data points as shown in the right-hand side at step 362.

Similarly, at step 363 consider that the support vectors are linear inseparable data and the first AI model (181ae) uses a kernel trick to transform an input space to a higher dimensional space as shown at step 364. The data points are plotted on the x-axis and z-axis when the linear inseparable data are used as support vectors.

Figure 3F:
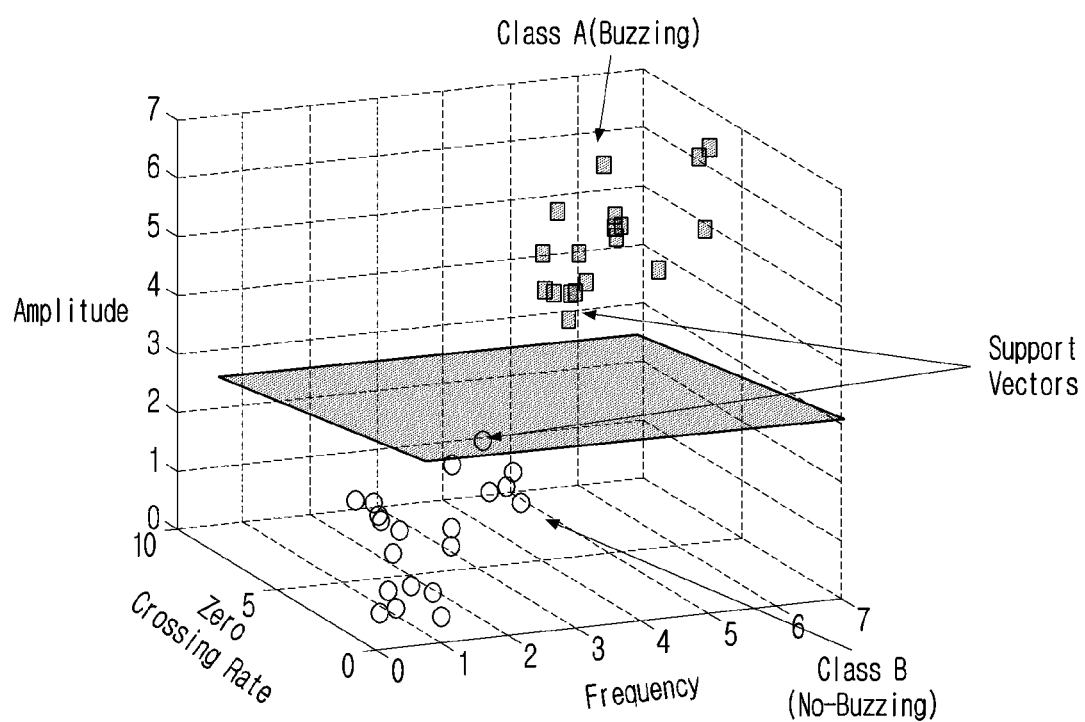
FIG. 3F illustrates a three dimensional representation of support vectors by the first AI model for detecting the buzzing sound, according to an embodiment as disclosed herein.

FIG. 3F illustrates a three dimensional representation of the support vectors by the first AI model (181ae) for detecting the buzzing sound, according to one or more embodiments herein.

Referring to the FIG. 3F, in the SVM algorithm the target is to maximize the margin between the data points and the hyperplane. The loss function that maximizes the margin is hinge loss:

$$c(x, y, f(x)) = \begin{cases} 0, & \text{if } y*(x) \geq 1 \\ 1 - y*f(x), & \text{else} \end{cases}$$

Further, a regularization parameter i.e., cost function is added. The objective of the regularization parameter is to balance the margin maximization and loss.

The cost function is:

$$\min_w \lambda \|w\|^2 + \sum_{i=1}^{n}(1 - y_i \langle x_i, w \rangle)_+$$

Partial derivatives are taken with respect to the weights to find the gradients. Using the gradients, the weights are updated:

$$\frac{\delta}{\delta w_k} \lambda \|w\|^2 = 2\lambda w_k$$

$$\frac{\delta}{\delta w_k}(1 - y_i \langle x_i, w \rangle)_+ = \begin{cases} 0, & \text{if } y_i \langle x_i, w \rangle \geq 1 \\ -y_i x_{ik} & \text{else} \end{cases}$$

When there is no misclassification $w = w - \alpha \cdot (2\lambda w)$

Figure 4A:
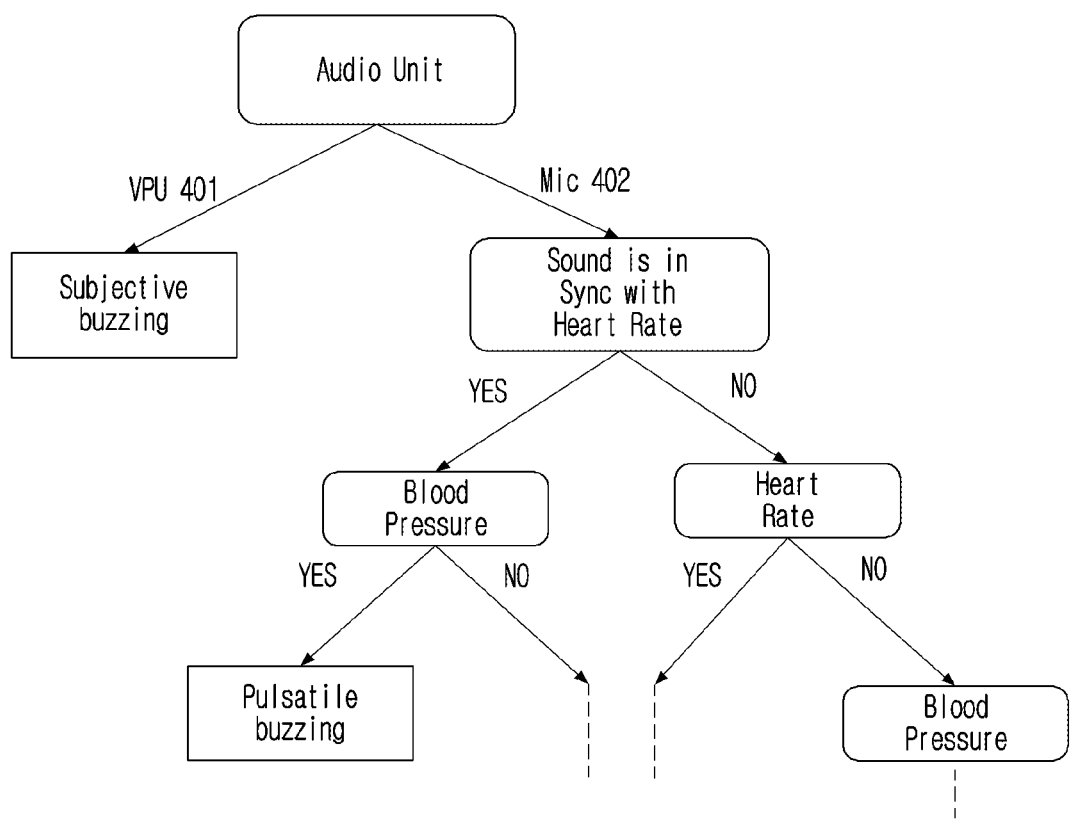
FIG. 4A illustrates a working of a buzzing classifier, according to an embodiment as disclosed herein.

Gradient Update:
When there is misclassification $w = w + \alpha \cdot (\mathcal{Y}_i \cdot x_i - 2\lambda w)$ Gradient Update:

FIG. 4A illustrates a working of the buzzing classifier (181b), according to an embodiment as disclosed herein.

Referring to the FIG. 4A, the buzzing sound is classified as the subjective buzzing and the objective nuzzling based on the audio content delivery device (100). The audio content delivery device (100) includes microphones 402 which detect the external sounds and reduces the noise by active noise cancellation. The microphones 402 facilitate delivering the audio content without any background noise. The audio content delivery device (100) also includes Voice Pickup Unit (VPU) 401 which senses when jaw (sound from internal bones) is moving. Further, as the jaw vibrates the VPU 401 converts data associated with the jaw movement to voice signals to enhance sound quality.

Further, the objective buzzing sound is classified as the pulsatile and the non-pulsatile based on other parameters such as the heart rate and the blood pressure of the user (as indicated in table. 1).

TABLE 1

| Heart Rate | Blood Pressure | Audio Unit | Output |
|---|---|---|---|
| High | High | 0 | Subjective |
| High | Low | 0 | Subjective |
| Low | High | 0 | Subjective |
| Low | Low | 0 | Subjective |
| High | Low | 1 | Objective |
| Low | High | 1 | Objective |
| High | High | 1 | Objective-Pulsatile |

The subjective buzzing sound is a sound in absence of real source from a body. The subjective buzzing sound causes inner ear hearing loss resulting in electrical signal abnormality and perception of sound. Sounds like ringing, hissing, static crickets, roaring, pulsing waves may be termed as the subjective buzzing sound. The subjective buzzing sound is possible to pickup with VPU of ear buds live (due to bone conduction). The subjective buzzing sound can occur due to exposure to loud noise (like bomb explosion, guns firing etc.), aging, head injuries, hearing loss etc. The objective buzzing sound is a real sound generated by the body. Pulsing noise due to high blood pressure, arterial or venomous growth or abnormal anomaly, small muscle spasm in ear or mouth. Sounds like intermittent series of sharp regular clicks or fairly regular continuous clicking sounds. The objective buzzing sound is possible to detect with external microphone 402 of the audio content delivery device 100 (because sound is audible). The objective buzzing sound can occur due to increase in blood flow rate, vibration in ear, overused muscle.

Figure 4B:
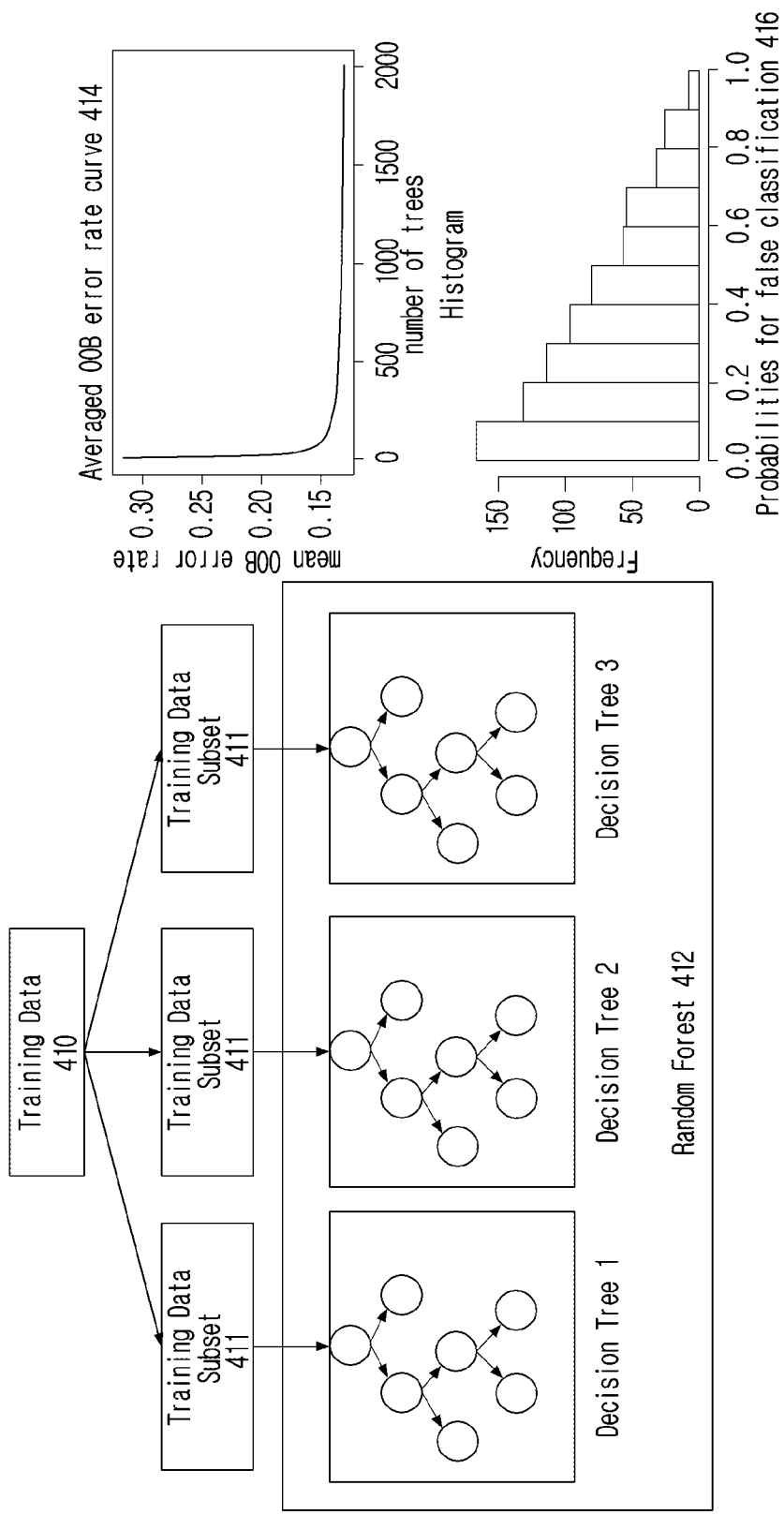
FIG. 4B illustrates a classification of the buzzing sound by the buzzing classifier, according to an embodiment as disclosed herein.

FIG. 4B illustrates a classification of the buzzing by the buzzing classifier (181*b*), according to an embodiment as disclosed herein.

Referring to the FIG. 4B, a multiple-rule based classifier 412, such as random forests algorithm, is used to learn/train from the dataset 410. The multi-rule based classifier 412, in some embodiments, includes 50, 60, 100, etc. or any other number of individual classifiers (e.g., decision trees). In one or more embodiments, the training dataset 410 is divided into several subsets 411, each subset 411 used by respective classifier (e.g., decision tree) in the multiple-rule based classifier 412. The outputs of the multiple trees are used to predict the output based on different weightage from the different trees' output.

Feature Selection Methods:

$$\text{Gini} = 1 - \Sigma_{j=1}^{c} p_j^2$$

$$\text{Entropy} = -\Sigma_{j=1}^{c} p_j \log p_j$$

Out-of-bag (OOB) error, also called out-of-bag estimate, is a method of measuring the prediction error of random forests, i.e., the multiple rule based classifier 412. An averaged OOB error rate curve 414 and probabilities of false classification graphs 416 are also illustrated in the FIG. 4B.

FIG. 5A illustrates a multiple regression model used to determine the user experience score by the user experience management controller (182*a*), according to an embodiment as disclosed herein.

Referring to the FIG. 5A, the user experience management controller (182*a*) is configured to determine multiple parameters associated with the buzzing sound and the user such as for example but not limited to an age of the user, an ear type of the user, emotional index of the user, a duration of the buzzing sound, an amplitude of the buzzing sound and noise pollution. The multiple parameters include dependent variables 501 and independent variables 502. The multiple parameters associated with the buzzing sound and the user are then fed to the multiple regression model of the user experience management controller (182*a*) to determine the impact score which can be referred to as a magnitude of the buzzing sound. Further, the user experience score is determined using the impact score as:

User experience score = 1 − impact score

Multiple example scenarios of the user experience score determined using the multiple parameters is provided in the table. 2.

TABLE 2

| Ear Type | External Noise (in dB) | Emotional Index | Buzzing duration (in mins) | Amplitude (in dB) | User age (in yrs) | Magnitude | User Experience (1-Magnitude) |
|---|---|---|---|---|---|---|---|
| 1 | 71 | 0.03 | 20 | 7 | 22 | 0.11 | 0.89 |
| 2 | 66 | 0.13 | 24 | 13 | 32 | 0.19 | 0.81 |
| 1 | 100 | 0.09 | 50 | 15 | 42 | 0.48 | 0.52 |
| 2 | 92 | 0.14 | 56 | 18 | 62 | 0.43 | 0.57 |
| 1 | 75 | 0.58 | 360 | 20 | 41 | 0.51 | 0.49 |
| 1 | 95 | 0.02 | 150 | 11 | 21 | 0.21 | 0.79 |
| 2 | 98 | 0.81 | 1440 | 28 | 72 | 0.93 | 0.07 |
| 2 | 96 | 0.64 | 600 | 25 | 59 | 0.75 | 0.25 |
| 2 | 93 | 0.58 | 720 | 22 | 47 | 0.61 | 0.39 |
| 2 | 94 | 0.74 | 1360 | 23 | 68 | 0.87 | 0.13 |

Further, the user experience management controller (182*a*) also minimizes a root mean square Error to attain higher accuracy as:

$$RMSE = \sqrt{\sum_{i=1}^{n} \frac{(\hat{y}_i - y_i)^2}{n}}$$

Figure 5B:
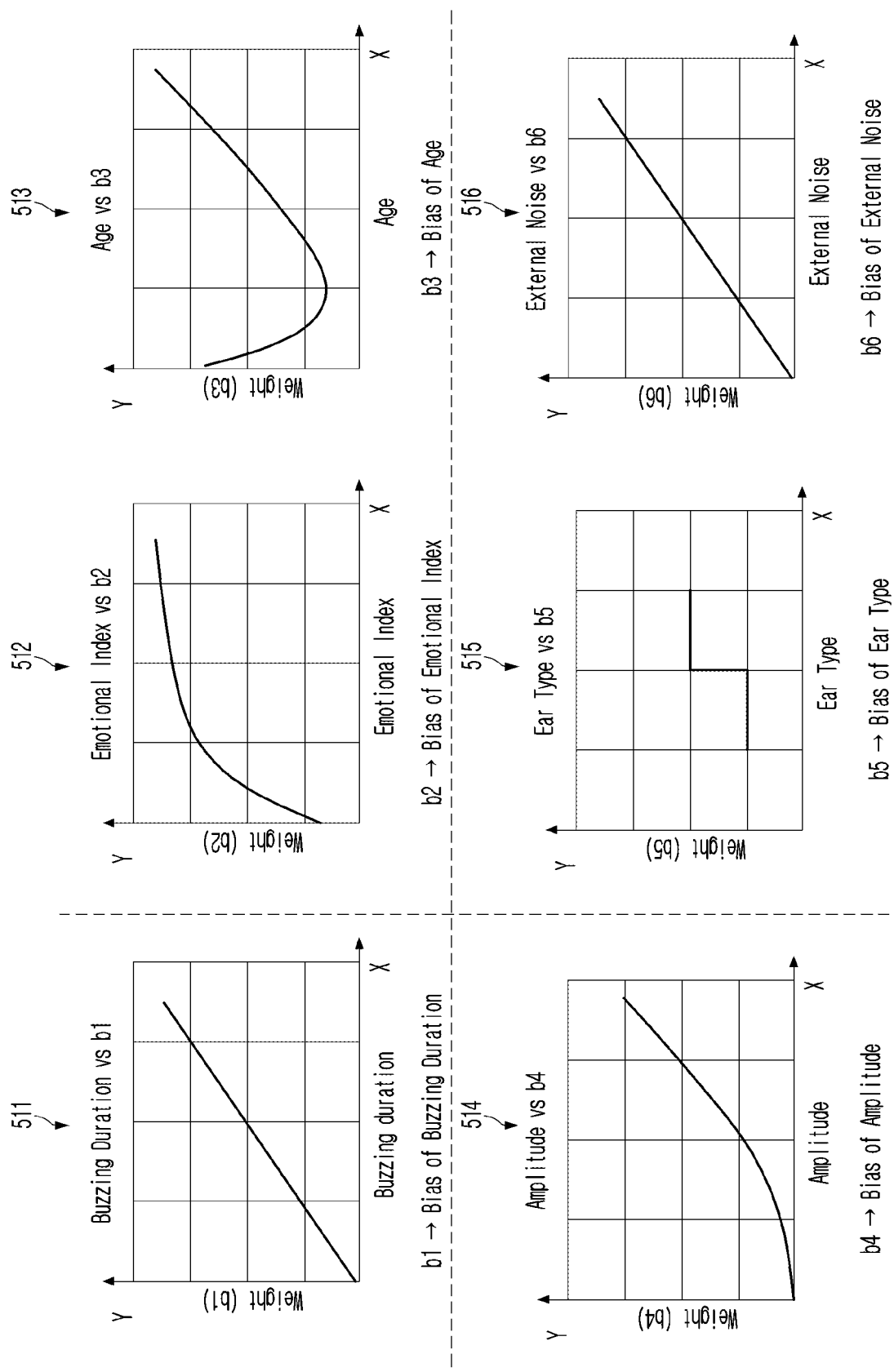
FIG. 5B are graph plots illustrating weight of each of plurality of parameters used in determining an impact score by the user experience management controller, according to an embodiment as disclosed herein.

FIG. 5B depicts graph plots illustrating weight of each of the plurality of parameters used in determining the impact score by the user experience management controller (182*a*), according to an embodiment as disclosed herein.

Referring to the FIG. 5B, a graph plot 511 depicts the buzzing duration on X-axis and weight (bias of the buzzing duration) on Y-axis. The buzzing duration is directly proportional to the weight in the impact score. Further, a graph plot 512 of the emotional index on X-axis and weight (bias of the emotional index) on Y-axis is shown. A graph plot 513 of the age of the user on X-axis and weight (bias of the age of the user) on Y-axis is also shown.

Additionally, a graph plot 514 of the amplitude of the buzzing sound on X-axis and weight (bias of the amplitude of the buzzing sound) on Y-axis is shown. The amplitude of the buzzing sound is exponentially proportional to the weight in the impact score. A graph plot 515 of the ear type of the user on X-axis and weight (bias of the ear type of the user) on Y-axis, and a graph plot 516 of the external noise/noise pollution on X-axis and weight (bias of the external noise/noise pollution) on Y-axis are also shown. The external noise/noise pollution is directly proportional to the weight in the impact score. It is understood that other parameters and combinations of parameters are used in other embodiments than those shown and listed herein.

Figure 6A:
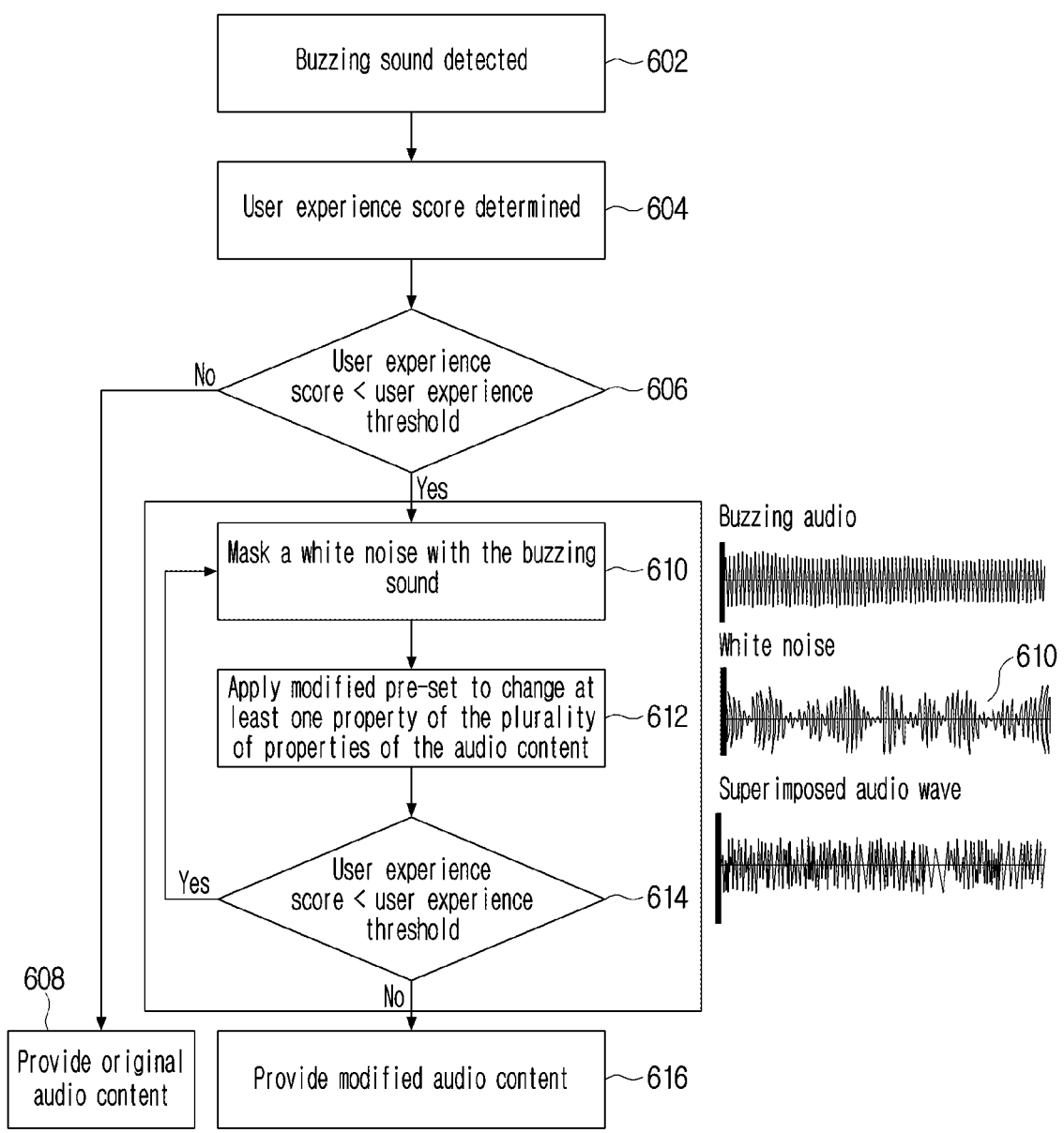
FIG. 6A is a flow chart illustrating a method for modifying an audio content based on properties of the buzzing sound and properties of audio content, according to an embodiment as disclosed herein.

FIG. 6A is a flow chart illustrating a method for modifying the audio content based on properties of the buzzing sound and the properties of audio content, according to an embodiment as disclosed herein.

Referring to the FIG. 6A, at step 602, the buzzing sound is detected and at step 604 the user experience score is determined for the detected buzzing sound. At step 606, the suppression controller (182*b*) determines whether the user experience score is less than the user experience threshold. The user experience threshold can be a predetermined value. Alternatively, or in addition, the user experience threshold can be dynamically adjusted. For example consider that the user experience threshold is 0.9. At step 608, the original audio content is provided to the user, on determining that the user experience score is not less than the user experience threshold (i.e., the user experience threshold is satisfied by the audio content, and hence, no modification is required).

On determining that the user experience score is less than the user experience threshold, the suppression controller (182b) at step 610 generates a white noise based on the properties of the buzzing sound and the properties of audio content and masks the buzzing sound with the white noise. Further, at step 612, the suppression controller (182b) applies the modified pre-set to change at least one of the plurality of properties of the audio content. The modified pre-set is determined such that the audio output to the user provides a soothing effect and is not harsh on the ears of the user.

At step 614, the suppression controller (182b) again determines if the user experience score is less than the user experience threshold. If the user experience score improves to be greater than the user experience threshold the modified audio content is provided to the user (at step 616). If the user experience score is still less than the user experience threshold, then the suppression controller (182b) loops to the step 610 to further modify the audio content.

Accordingly, the suppression controller (182b) ensures that the audio content provided to the user is above the user experience threshold by modifying the audio content until to modify the user experience score satisfies the user experience threshold.

Figure 6B:
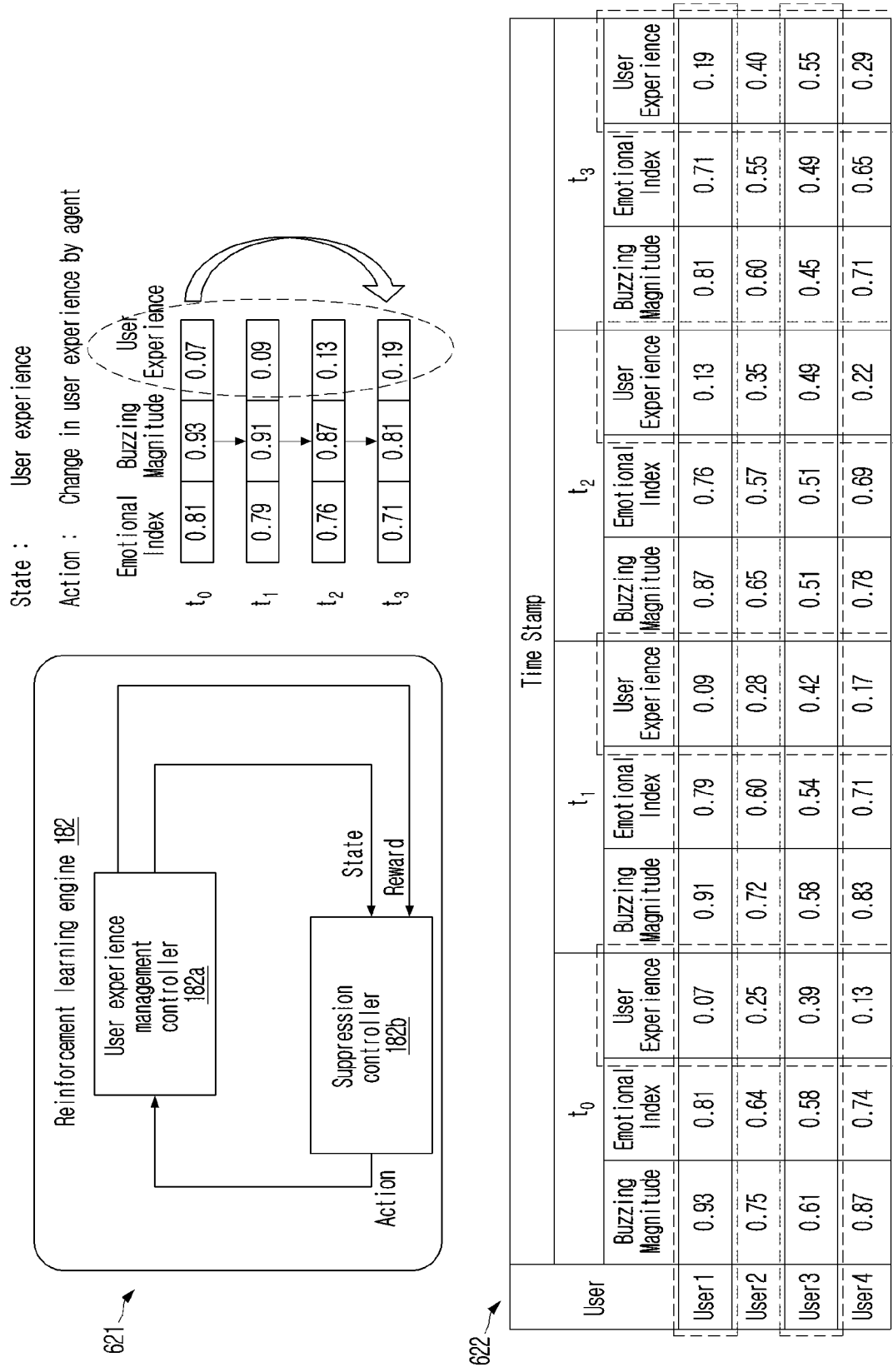
FIG. 6B illustrates sample dataset and working of a reinforcement learning engine, according to an embodiment as disclosed herein.

FIG. 6B illustrates sample dataset and working of the reinforcement learning engine (182), according to an embodiment as disclosed herein.

Referring to the FIG. 6B, at 621, a state diagram of the reinforcement learning engine (182) is provided. The reinforcement learning engine (182) includes the user experience management controller (182a) and the suppression controller (182b). The state from the user experience management controller (182a) is fed to the suppression controller (182b) based on which the suppression controller (182b) determines the action such as masking buzzing sound with the white noise. Further, due to the action performed by the suppression controller (182b) iteratively, the user experience score improves and the user experience management controller (182a) provides the outputs to the suppression controller (182b).

A table of time stamps 622 of the performance of the reinforcement learning engine (182) with respect to multiple users is provided which also shows the improvement of the user experience score over a period of time for each user.

Figure 6C:
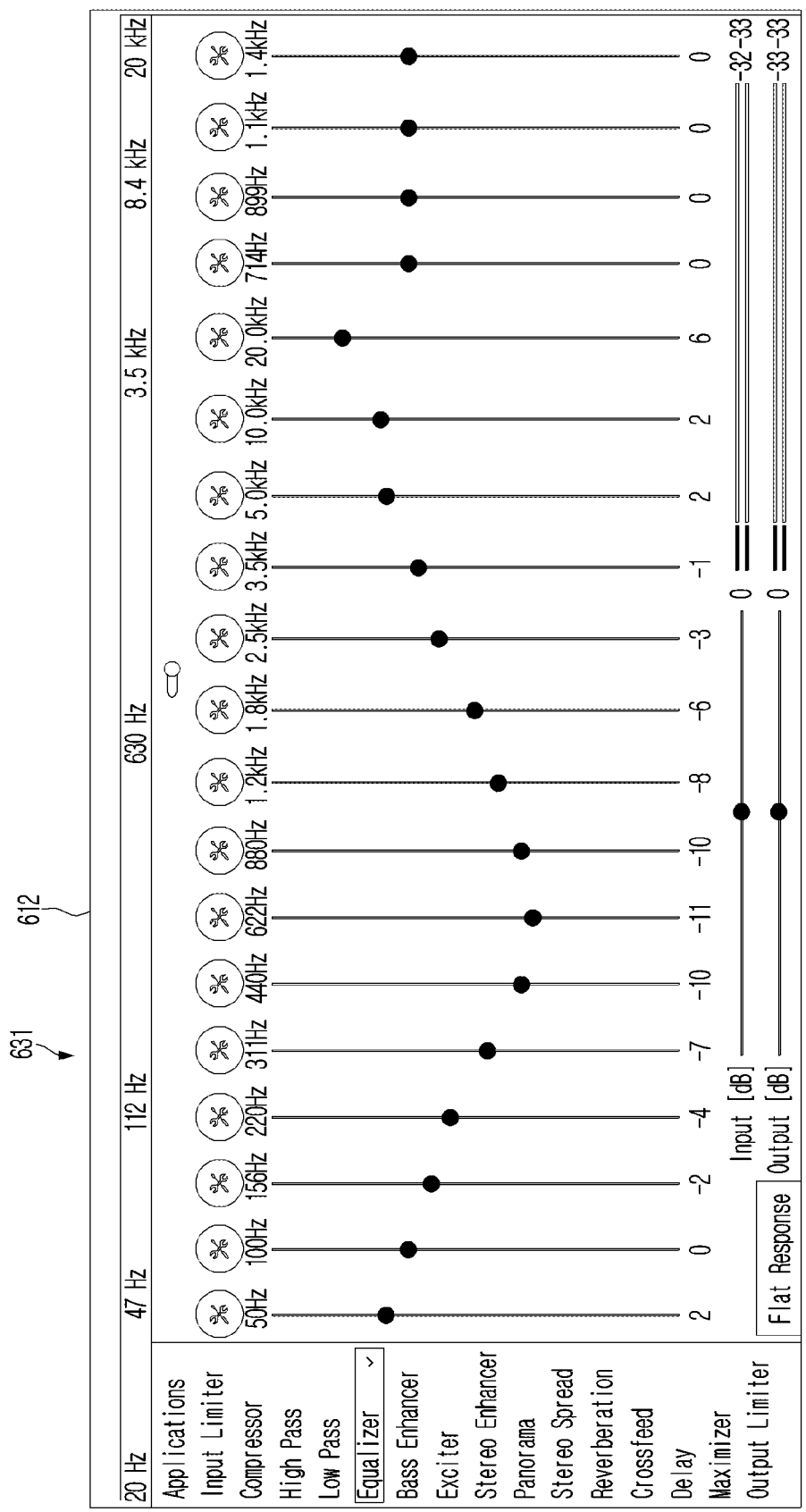
FIG. 6C illustrates modified pre-sets to be applied by a suppression controller to the audio content to improve the user experience score, according to an embodiment as disclosed herein.
Figure 6D:
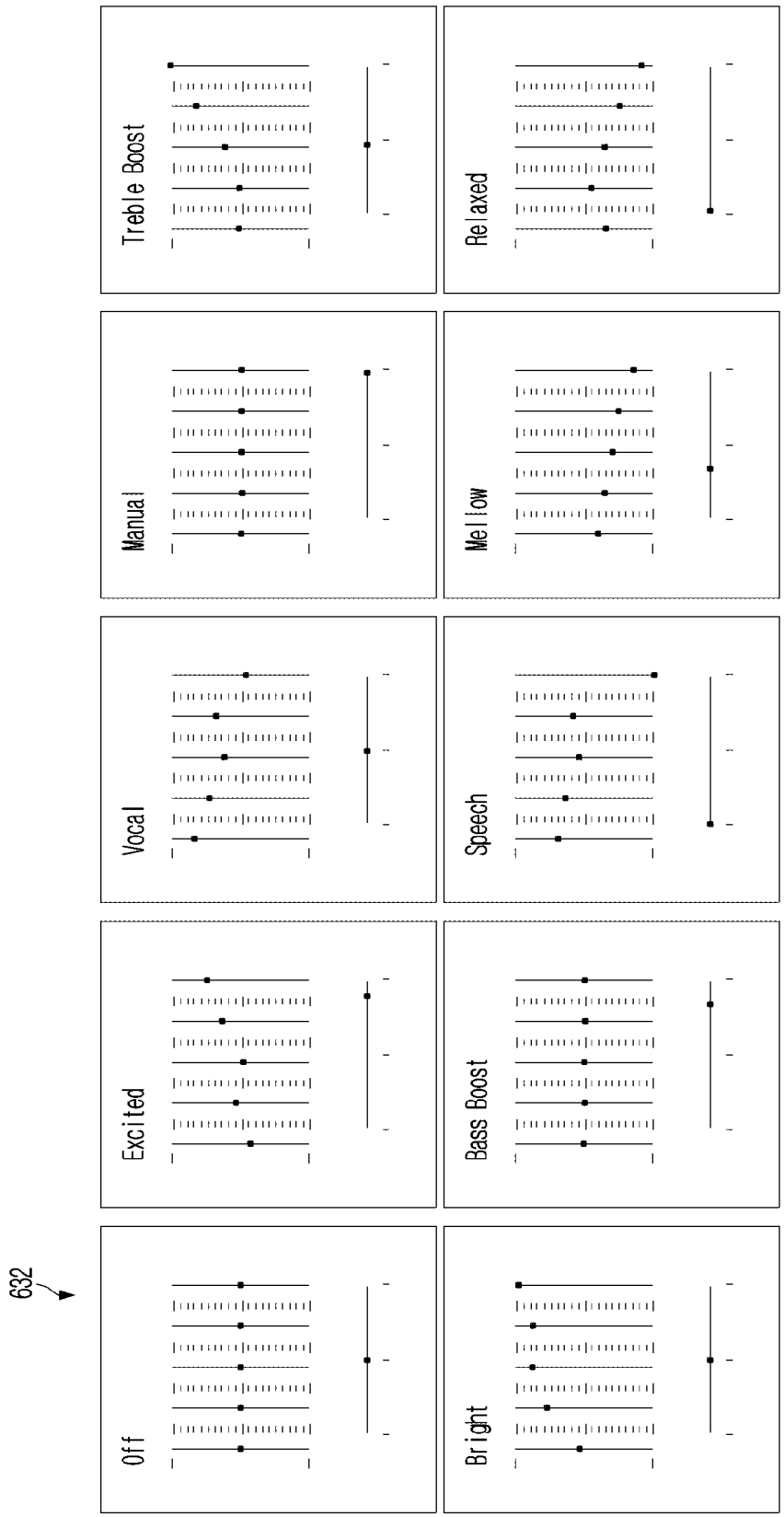
FIG. 6D illustrates modified pre-sets to be applied by a suppression controller to the audio content to improve the user experience score, according to an embodiment as disclosed herein.

FIG. 6C and FIG. 6D illustrate pre-sets to be applied by the suppression controller (182b) to the audio content to improve the user experience score, according to an embodiment as disclosed herein. In one or more embodiments, the pre-sets are modified by the suppression controller (182b).

Referring to the FIG. 6C and FIG. 6D, the modified pre-sets to be applied by the suppression controller (182b) to the audio content to improve the user experience score are determined. The data of different frequency bands are obtained and using the different frequency bands the modified pre-sets are created to improve the user experience, as shown in step 631 (FIG. 6C). Out of the mentioned frequency bands, 5 bands are selected and used for modification to improve the user experience. In some embodiments, the frequency bands that are included in the pre-set are 50 Hz, 100 Hz, 156 Hz, 220 Hz, 311 Hz, 440 Hz, 622 Hz, 880 Hz, 1.2 kHz, 1.8 kHz, 2.5 kHz, 3.5 kHz, 6.3 kHz, 16.0 kHz, 20.0 kHz, 714 Hz, 899 Hz, 1.1 kHz, 1.4 kHz. it is understood that different number of frequency bands, and/or different frequency bands than those shown here can be used in other embodiments.

At step 632 (FIG. 6D), different pre-sets are determined by changing audio properties. By using reinforcement learning, the user experience score can be improved by applying different pre-sets and masking audio wave with some white noise.

Figure 7A:
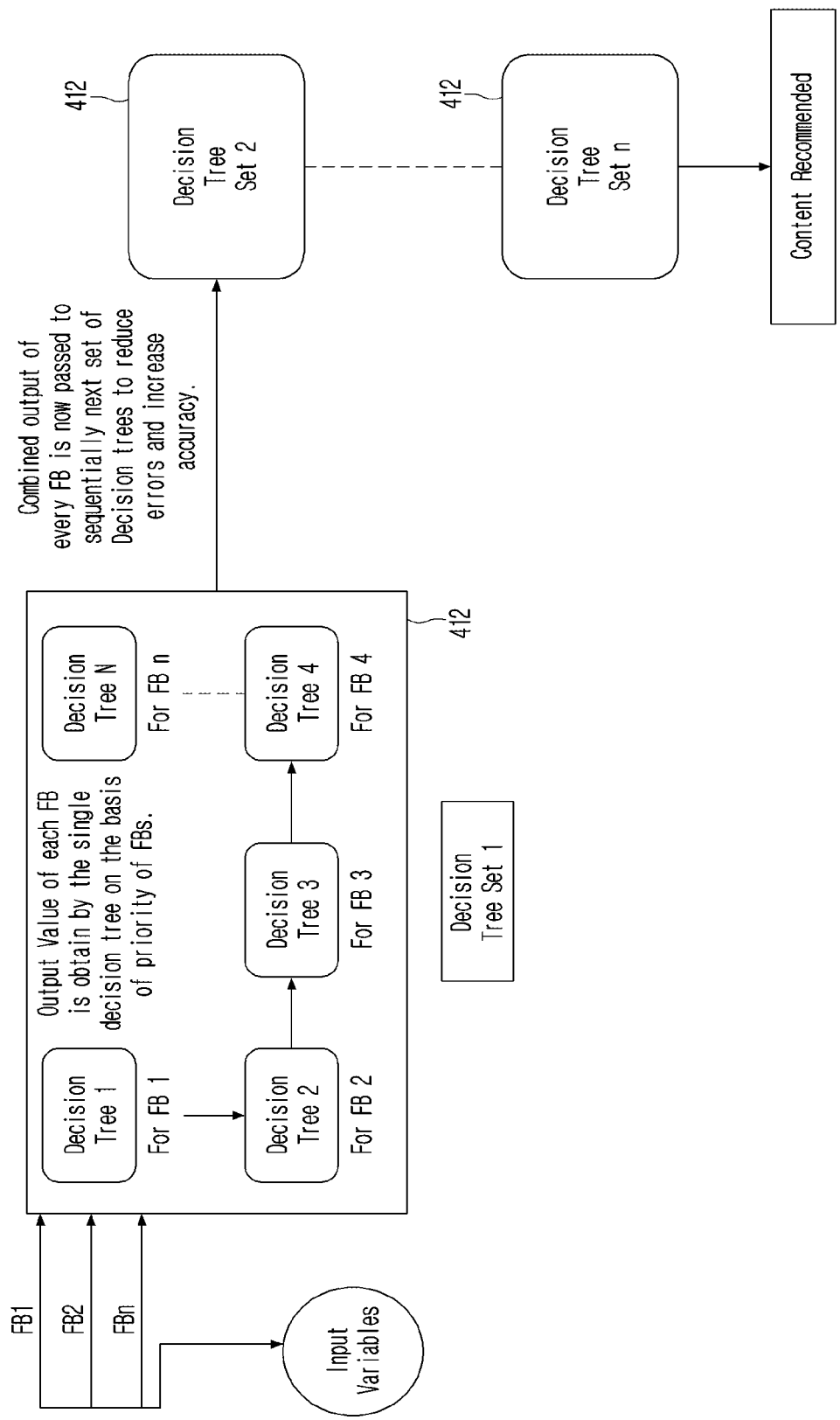
FIG. 7A illustrates a plurality of decision trees used for determining a priority value for plurality of audio content based on audio pre-set values by a content recommendation controller, according to the embodiments as disclosed herein.

FIG. 7A illustrates a plurality of decision trees used for determining a priority value for the plurality of audio content based on the audio pre-set values by the content recommendation controller (186), according to the embodiments as disclosed herein.

The content recommendation controller (186) determines multiple audio pre-set values corresponding to the multiple audio content using a multi-rule classifier 412, for example, a random forest including a plurality of decision trees. In some embodiments, the plurality of audio pre-set values is determined using a set of n decision trees, where n is the count of frequency bandwidths. For example the frequency bandwidths may include one or more of 50 Hz, 100 Hz, 156 Hz, 220 Hz, 311 Hz, 440 Hz, 622 Hz, 880 Hz, 1.2 kHz, 1.8 kHz, 2.5 kHz, 3.5 kHz, 6.3 kHz, 16.0 kHz, 20.0 kHz, 714 Hz, 899 Hz, 1.1 kHz, 1.4 kHz, and the like. The multiple audio contents may be stored in the electronic device associated with the audio content delivery device (100) or in a remote server. In some embodiments, a plurality of multi-rule classifiers 412 are used in which output from a first classifier 412 is provided to a second classifier 412, and so on to reduce errors and increase accuracy. Each classifier 412 is a set of decision trees in some embodiments, where random forests are used as classifiers. It is understood that in other embodiments, the classifiers can be implemented using techniques other than random forest. Based on the output of the one or more classifiers, an audio content is recommended to the user.

Figure 7B:
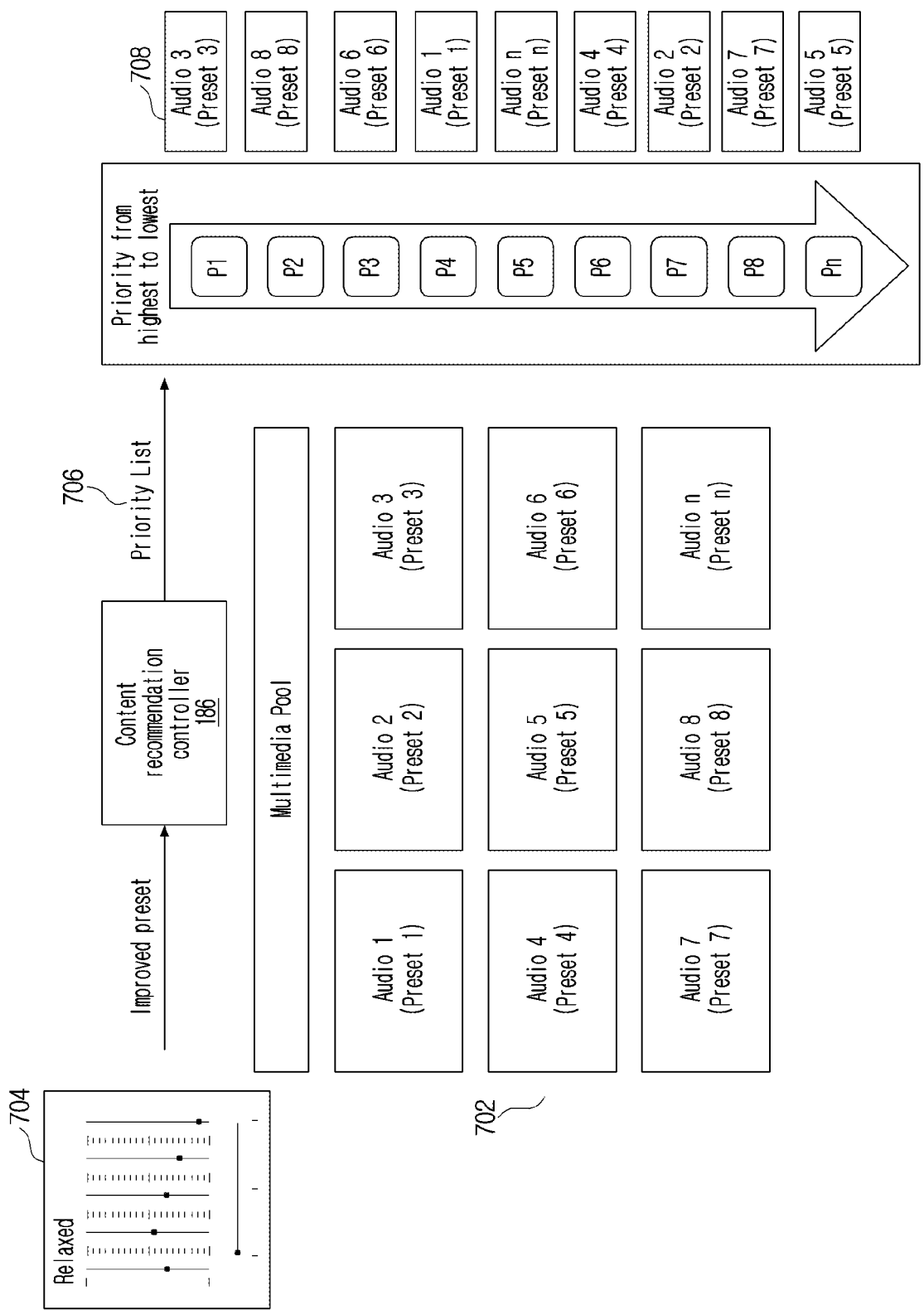
FIG. 7B illustrates recommending the audio content based on a priority value to the user by the content recommendation controller, according to the embodiments as disclosed herein.

FIG. 7B illustrates recommending the audio content based on the priority value corresponding to the user as determined by the content recommendation controller (186), according to the embodiments as disclosed herein.

Referring to the FIG. 7B, at step 702 consider the multiple audio content available in the multimedia pool in the order of their occurrence. At step 704, the content recommendation controller (186) receives at least one of the improved pre-sets as input. Further, at step 706 the content recommendation controller (186) determines a resemblance between the improved pre-set and the pre-set of at least one of the multiple audio content available in the multimedia pool. Further, at step 708 the content recommendation controller (186) assigns a priority value for each of the plurality of audio content based on the resemblance between the improved pre-set and the pre-set of the audio content, and the user experience score. In an embodiment, the priority value indicates an order in which the audio content will be played to reduce the occurrence of the buzzing sound or reduces the effect of the buzzing sound in the user's ear. In another embodiment, the priority value indicates an order in which the audio content will be recommended to the user and played based on user preference or user input.

Figure 8A:
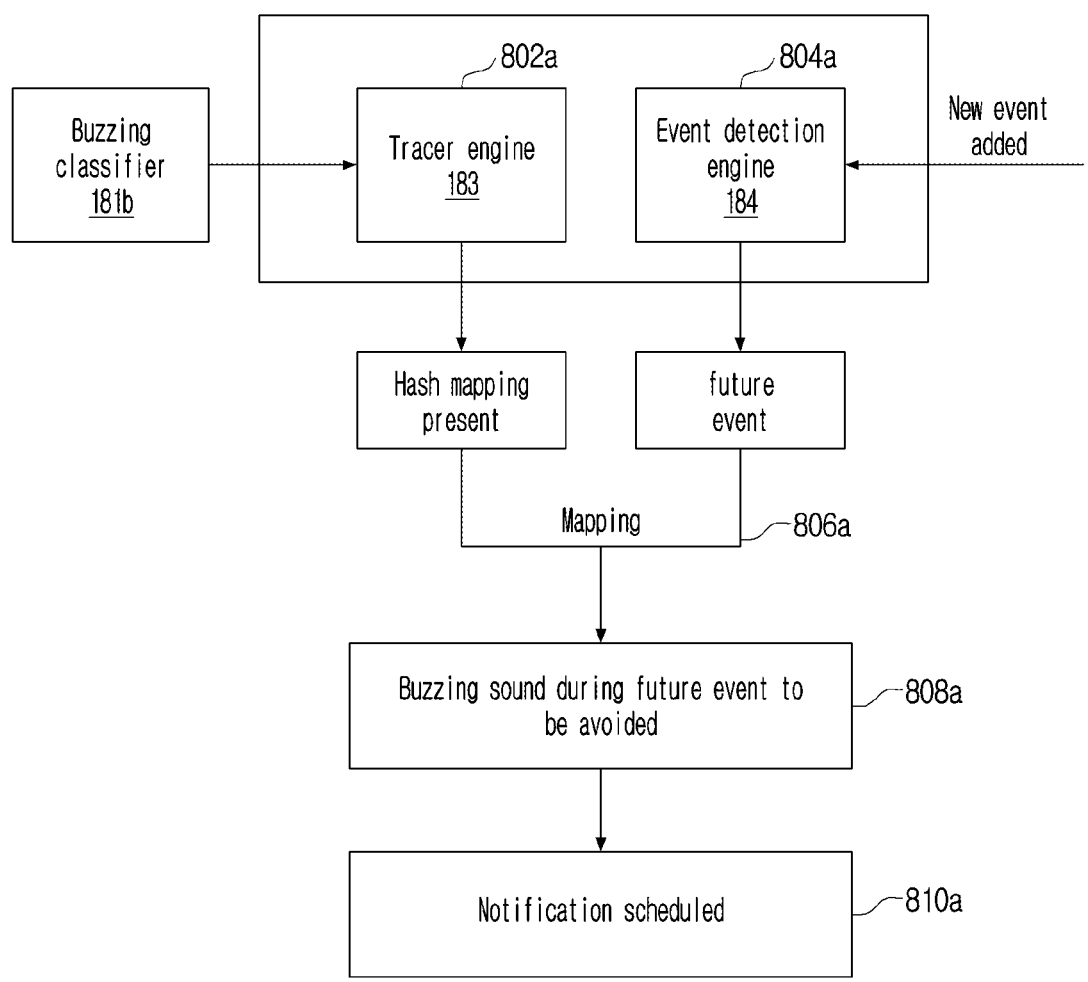
FIG. 8A is a flow chart illustrating a method for providing notification by the audio content delivery device based on a future event to avoid the buzzing sound, according to the embodiments as disclosed herein.

FIG. 8A is a flow chart illustrating a method for providing notification by the audio content delivery device (100) based on the future event to avoid the buzzing sound, according to the embodiments as disclosed herein.

Referring to the FIG. 8A, at step 802a, the tracer engine (183) receives the properties of the buzzing sound as classified by the buzzing classifier (181b). At step 804a, the event detection engine (184) identifies and adds a new event which is scheduled to occur at a future point in time. At step 806*a*, the audio content delivery device (100) creates a mapping between a hash value indicating the properties of the buzzing sound and a future event. Further, at step 808*a*, the audio content delivery device (100) determines the buzzing sound which is to be avoided during the future event. At step 810*a*, the audio content delivery device (100) schedules a notification for avoiding the buzzing sound. The notification may be an indication for the user to put on the audio content delivery device (100) before the future event. Alternatively, or in addition, the notification informs the user of the prediction of the buzzing sound because of the future event and also to avoid doing specific things, or to take certain actions to prevent/minimize the effect of the buzzing sound, etc.

FIG. 8B is an example of event detection and management of the audio content delivery by the audio content delivery device (100), according to the embodiments as disclosed herein.

Consider that at step 802*b*, the tracer engine (183) has recorded four different sets of buzzing sounds along with the properties of each of the buzzing sound. For example, set 1 includes the buzzing sound with properties such as type is subjective, number of times the buzzing sound has occurred is 2, an average duration of the buzzing sound is 175 minutes, ear count is 2, an average frequency of the buzzing sound is 0.404, an average amplitude of the buzzing sound is 0.361 and the root cause for the occurrence of the buzzing sound is air pressure and noise pollution. Similarly, a set 2, a set 3 and a set 4 of the buzzing sounds along with the corresponding properties associated are available in the tracer engine (183). At step 804*b* consider that a list of future events available in the electronic device (1000) of the user is empty. At step 806*b*, the user books an airline ticket and at step 808*b*, the air flight journey is stored in the list of future events available in the electronic device (1000) of the user. Similarly, at step 810*b* the user books a movie ticket using the electronic device (1000) which is stored in the list of future events available in the electronic device (1000) of the user (in step 812*b*). It should be noted that in some embodiments the booking of the airline ticket (808*b*) and the booking of the movie ticket (810*b*) may be performed independent of the electronic device 1000, and that the electronic device 1000 receives an indication of such events, i.e., the bookings, via a communication accessible by the electronic device 1000, e.g., email, text message, instant message, etc. Further, it should be noted that while examples herein describe an air flight and a movie, the technical solutions herein are not limited to such events. Rather, the technical solutions herein can be used to avert buzzing sound during a travel (by bus, car, train, air, etc.), movies, concerts, sports events, etc., or any other event at which the audio content delivery device predicts a buzzing sound for the user.

Figure 8C:
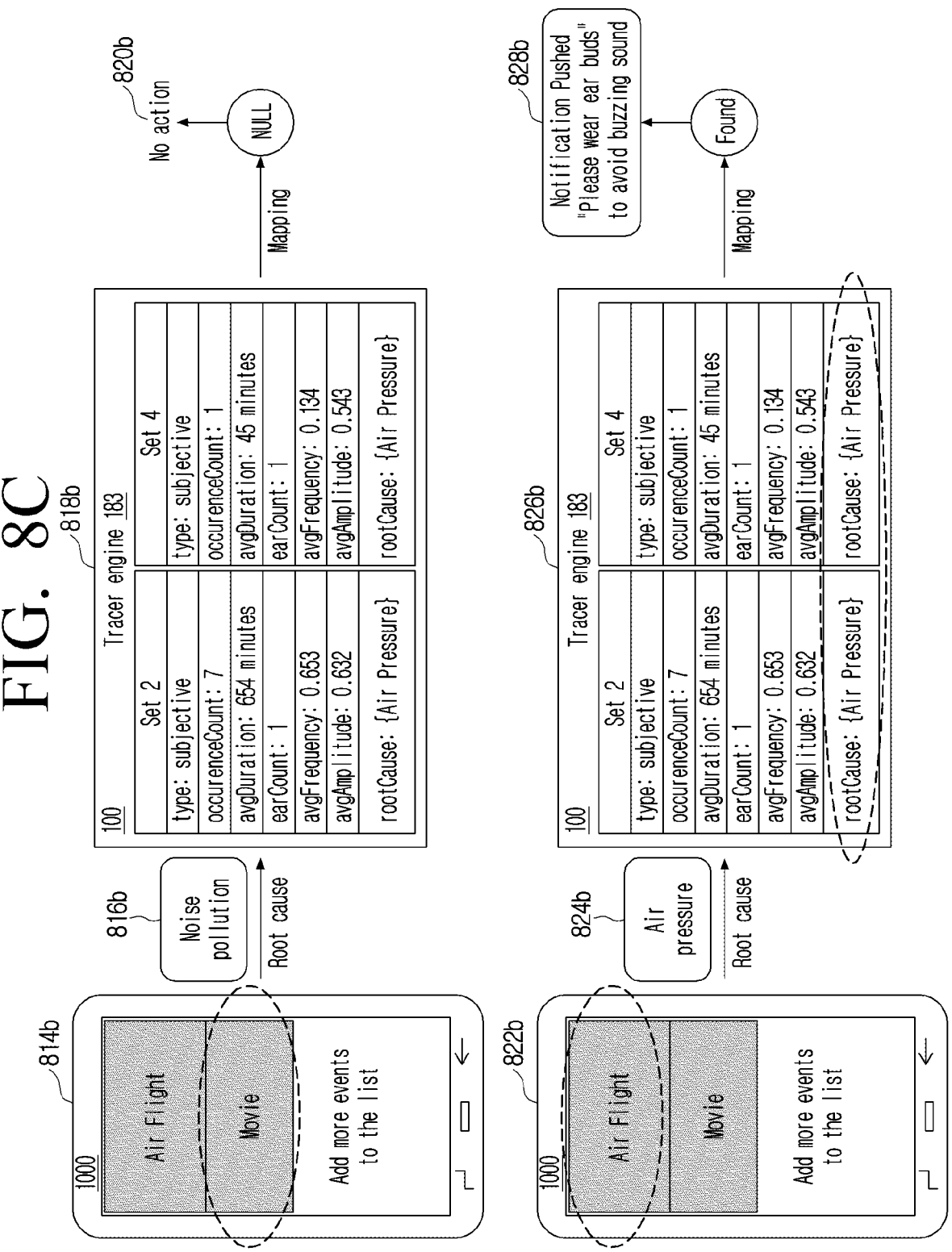
FIG. 8C is an example of event detection and management of the audio content delivery by the audio content delivery device, according to the embodiments as disclosed herein.

FIG. 8C is an example of event detection and management of the audio content delivery by the audio content delivery device (100), according to the embodiments as disclosed herein.

Referring to FIG. 8C, at step 814*b*, consider that the scheduled event of the movie occurs and the audio content delivery device (100) determines the event occurring. At step 816*b*, the audio content delivery device (100) determines the root cause of the buzzing sound in the movie as "noise pollution". Because the two related buzzing sounds associated with the event in the tracer engine (183) do not have the root cause as "noise pollution", there is no mapping found (step 820*b*). Because there is no mapping found there is no action taken by the audio content delivery device (100) in this case.

Consider another scenario of the event in the list of future events occurring e.g., the user traveling by airline (step 822*b*). At step 824*b*, the audio content delivery device (100) determines the root cause of the buzzing sound in the movie as "air pressure". Two related buzzing sounds associated with the event in the tracer engine (183) maps with the root cause "air pressure" (826*b*). Further, at step 828*b*, the audio content delivery device (100) provides a notification on the electronic device (1000) as "Please wear ear buds" to avoid the buzzing sound when the user boards the airline. Further, once the user puts on the audio content delivery device (100), the white noise is automatically generated and provided to the user to avoid the buzzing sound.

Therefore, unlike existing methods and systems, the audio content delivery device (100) using technical solutions herein automatically determines the future event and pushes a notification to caution the user to put on the audio content delivery device (100) to avoid the buzzing sound. Also, based on the user history a white noise corresponding to the buzzing sound associated with the event is generated to provide a soothing experience to the user, and minimize the effect of the buzzing sound.

In another example, consider that the user is continuously listening to loud music on the audio content delivery device (100) which has led the user to experience ear pain and/or headache. In existing methods and systems, the user has to manually reduce the volume of the music or continue suffering the pain. The technical solutions herein facilitate the audio content delivery device (100) to intelligently determine that the user is listening to the loud music for more than a specific duration of time and automatically runs the suppression controller (182*b*) to generate the white noise. Here, the specific duration of time is particular to the user based on his/her history with buzzing sounds, aches, etc. as learned by the audio content device 100. Further, the suppression controller (182*b*) determines the improved pre-set which is soothing to the ear of the user and recommends a playlist comprising the music resembling the improved pre-set. Here, the improved pre-set includes one or more audio content, e.g., frequency bands, that can result in soothing the user. The recommended playlist includes one or more audio content that resembles the improved pre-sets. Accordingly, in response to the user selecting and playing the music from the recommended playlist, the user can reduce the ear pain and/or headache. In some embodiments, the recommended playlist may be selected and played automatically.

In another example, the audio content delivery device (100) determines the buzzing sound experienced by the user and provides the notification every time the buzzing sound is detected. Further, when the number of times the buzzing sound occurs crosses a certain threshold number, the audio content delivery device (100) may notify the electronic device (1000) associated with the user with a warning message indicating a severity of the buzzing sound and also advice the user to consult a trained medical practitioner to address the same. The threshold number can be a predetermined number and/or dynamically adjusted for the user.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the scope of the embodiments as described herein.

The invention claimed is:

1. A method for managing audio content delivery by an audio content delivery device, the method comprising:
    determining, by the audio content delivery device, occurrence of a buzzing sound in at least one ear of a user in response to outputting an audio content;
    categorizing, by the audio content delivery device, the buzzing sound as one of a subjective buzzing or an objective buzzing;
    determining, by the audio content delivery device, a plurality of parameters associated with the buzzing sound and the user, wherein the plurality of parameters associated with the buzzing sound and the user comprises a duration of the buzzing sound and an amplitude of the buzzing sound;
    determining, by the audio content delivery device, an impact score based on the plurality of parameters associated with the buzzing sound and the user;
    determining, by the audio content delivery device, an impact of the buzzing sound on the user by computing a user experience score, the user experience score being related to the impact score;
    generating, by the audio content delivery device, a modified audio content based on properties of the buzzing sound and properties of the audio content,
    determining of the impact of the buzzing sound on the user comprising: comparing the user experience score and a user experience threshold, and modifying the audio content based on determining that the impact of the buzzing sound on the user is high, in response to determining that the user experience score is below the user experience threshold; and
    outputting, by the audio content delivery device, the modified audio content.

2. The method as claimed in claim 1, wherein determining, by the audio content delivery device, the occurrence of the buzzing sound in the at least one ear comprises:
    receiving, by the audio content delivery device, the audio content to be output in the at least one ear;
    extracting, by the audio content delivery device, a plurality of features of the audio content;
    obtaining, by the audio content delivery device, normalized values of each of the plurality of features by scaling the extracted plurality of features of the audio content;
    providing, by the audio content delivery device, the normalized values of each of the plurality of features as an input to a pre-trained first Artificial Intelligence (AI) model; and
    determining, by the audio content delivery device, the occurrence of the buzzing sound in the at least one ear based on an output of the pre-trained first AI model.

3. The method as claimed in claim 1, wherein the buzzing sound is categorized as one of the subjective buzzing or the objective buzzing based on a trained artificial intelligence model.

4. The method as claimed in claim 1, further comprising:
    determining, by the audio content delivery device, that the buzzing sound is categorized as the objective buzzing sound;
    determining, by the audio content delivery device, a heart rate and blood pressure of the user; and
    classifying, by the audio content delivery device, the objective buzzing sound as one of pulsatile buzzing or non-pulsatile buzzing based on the heart rate and the blood pressure of the user.

5. The method as claimed in claim 4, further comprising:
    determining, by the audio content delivery device, a plurality of properties of the buzzing sound; and
    storing, by the audio content delivery device, the plurality of properties of the categorized buzzing sound and user context.

6. The method as claimed in claim 1, wherein the plurality of parameters associated with the buzzing sound and the user comprises an age of the user, an ear type of the user, an emotional index of the user, an amplitude of noise pollution;
    wherein determining, by the audio content delivery device, the impact of the buzzing sound on the user comprises:
    determining, by the audio content delivery device, the user experience score using the impact score; and
    outputting the audio content without modification based on determining that the impact of the buzzing sound on the user is low, in response to determining that the user experience score is above the user experience threshold.

7. The method as claimed in claim 1, wherein modifying, by the audio content delivery device, the audio content comprises:
    masking the buzzing sound with a white noise, wherein the white noise is generated based on properties of the buzzing sound and properties of audio content, and
    applying at least one modified pre-set to change at least one property of the properties of the audio content.

8. The method as claimed in claim 7, further comprising:
    determining, by the audio content delivery device, a resemblance between the at least one modified pre-set and at least one new audio content of a plurality of audio contents in a playlist of the user; and
    reordering, by the audio content delivery device, priority of the at least one new audio content in the playlist of the user.

9. The method as claimed in claim 1, wherein outputting, by the audio content delivery device, the modified audio content comprises:
    identifying, by the audio content delivery device, at least one new audio content from a plurality of audio contents in a playlist based on the user experience score and the properties of the audio content being played; and
    providing, by the audio content delivery device, a recommendation of the at least one new audio content to the user.

10. The method as claimed in claim 1, further comprising:
    detecting, by the audio content delivery device, at least one event which causes the buzzing sound;
    providing, by the audio content delivery device, a suggestion to the user to put on the audio content delivery device; and
    generating, by the audio content delivery device, a white noise for averting the buzzing sound.

11. The method of claim 10, wherein the white noise is generated to mask the buzzing sound that is predicted to occur during the at least one event.

12. The method of claim 11, wherein the white noise is generated based on a plurality of properties associated with the buzzing sound, the plurality of properties determined based on a user history.

13. The method as claimed in claim 1, further comprising:
    detecting, by the audio content delivery device, at least one future event of the user;
    determining, by the audio content delivery device, the buzzing sound associated with the at least one future event and the properties of the buzzing sound associated with the at least one future event based on a user history; and
    providing, by the audio content delivery device, a notification on an electronic device of the user for averting the buzzing sound.

14. An audio content delivery device for managing audio content delivery, the audio content delivery device comprising:
    a memory;
    a processor coupled to the memory;
    a communicator coupled to the memory and the processor; and
    an audio content management controller coupled to the memory, the processor and the communicator, and configured to:
    detect a buzzing sound in a user's ear in response to outputting an audio content;
    categorize the buzzing sound as one of a subjective buzzing or an objective buzzing,
    determine a plurality of parameters associated with the buzzing sound and the user, wherein the plurality of parameters associated with the buzzing sound and the user comprises a duration of the buzzing sound and an amplitude of the buzzing sound;
    determine an impact score based on the plurality of parameters associated with the buzzing sound and the user,
    determine an impact of the buzzing sound on the user by computing a user experience score the user experience score being related to the impact score,
    determine of the impact of the buzzing sound on the user comprising: comparing the user experience score and a user experience threshold, and modifying the audio content based on determining that the impact of the buzzing sound on the user is high, in response to determining that the user experience score is below the user experience threshold,
    generating a modified audio content based on properties of the buzzing sound and properties of the audio content, and
    output the modified audio content on the audio content delivery device to the user.

15. The audio content delivery device as claimed in claim 14, wherein the audio content management controller, to detect the buzzing sound, is further configured to:
    receive the audio content to be output;
    extract a plurality of features of the audio content;
    obtain normalized values of each of the plurality of features by scaling the extracted plurality of features of the audio content;
    provide the normalized values of each of the plurality of features as an input to a pre-trained first Artificial Intelligence (AI) model; and
    determine the occurrence of the buzzing sound in the user's ear based on an output of the pre-trained first AI model.

* * * * *